(12) United States Patent
Bennett et al.

(10) Patent No.: US 9,757,122 B2
(45) Date of Patent: Sep. 12, 2017

(54) FASTENER

(71) Applicant: ZIPTEK LLC, Sarasota, FL (US)

(72) Inventors: William F Bennett, Sarasota, FL (US); Ramses Galaz Mendez, Sonora (MX); Daniel Francisco Gomez Romo, Sonora (MX)

(73) Assignee: Ziptek LLC, Sarasota, FL (US)

( * ) Notice: Subject to any disclaimer, the term of this patent is extended or adjusted under 35 U.S.C. 154(b) by 0 days.

(21) Appl. No.: 14/827,313

(22) Filed: Aug. 15, 2015

(65) Prior Publication Data

US 2015/0351740 A1 Dec. 10, 2015

Related U.S. Application Data

(62) Division of application No. 14/203,846, filed on Mar. 11, 2014.

(Continued)

(51) Int. Cl.
| | |
|---|---|
| *A61B 17/58* | (2006.01) |
| *A61B 17/60* | (2006.01) |
| *A61F 2/00* | (2006.01) |
| *A61B 17/06* | (2006.01) |
| *A61B 17/88* | (2006.01) |

(Continued)

(52) U.S. Cl.
CPC .... *A61B 17/06166* (2013.01); *A61B 17/0401* (2013.01); *A61B 17/0482* (2013.01); *A61B 17/0487* (2013.01); *A61B 17/8888* (2013.01); *A61F 2/0811* (2013.01); *A61B 17/0483* (2013.01); *A61B 17/0485* (2013.01); *A61B 17/06061* (2013.01); *A61B 2017/00526* (2013.01); *A61B 2017/044* (2013.01); *A61B 2017/0404* (2013.01); *A61B 2017/0406* (2013.01); *A61B 2017/0409* (2013.01); *A61B 2017/0414* (2013.01); *A61B 2017/0461* (2013.01); *A61B 2017/0464* (2013.01); *A61B 2017/0488* (2013.01); *A61B 2017/06176* (2013.01); *A61F 2002/0817* (2013.01); *A61F 2002/0858* (2013.01)

(58) Field of Classification Search
None
See application file for complete search history.

(56) References Cited

U.S. PATENT DOCUMENTS

| | | |
|---|---|---|
| 3,695,271 A | 10/1972 | Chodorow |
| 4,287,807 A | 9/1981 | Pacharis et al. |

(Continued)

FOREIGN PATENT DOCUMENTS

| | | |
|---|---|---|
| GB | 1506362 | 4/1976 |
| WO | WO 2012/058301 | 5/2012 |

(Continued)

*Primary Examiner* — Sameh Boles
(74) *Attorney, Agent, or Firm* — Frijouf, Rust & Pyle P.A.

(57) ABSTRACT

An apparatus and method is disclosed for securing tissue to a bone comprising a novel screw anchor for insertion into a bone by a novel rotational driver. The screw anchor and rotation driver enables the screw to be completely embedded into the bone while permitting a suture to be threaded through a transverse aperture in the screw. The rotation driver facilitates insertion and engagement of a capture with one of a series of protuberance formed along a length of a suture. In addition, the method is disclosed of forming the series of protuberance.

8 Claims, 14 Drawing Sheets

Related U.S. Application Data

(60) Provisional application No. 61/778,350, filed on Mar. 12, 2013.

(51) Int. Cl.
*A61F 2/08* (2006.01)
*A61B 17/04* (2006.01)
*A61B 17/00* (2006.01)

(56) References Cited

U.S. PATENT DOCUMENTS

| | | |
|---|---|---|
| 4,532,926 A | 8/1985 | O'Holla |
| 4,534,350 A | 8/1985 | Golden et al. |
| 4,667,675 A | 5/1987 | Davis |
| 4,669,473 A | 6/1987 | Richards et al. |
| 4,741,330 A | 5/1988 | Hayhurst |
| 4,796,612 A | 1/1989 | Reese |
| 4,898,156 A | 2/1990 | Gatturna et al. |
| 4,950,285 A | 8/1990 | Wilk |
| 5,047,034 A | 9/1991 | Sohngen |
| 5,053,047 A | 10/1991 | Yoon |
| 5,163,940 A | 11/1992 | Bourque |
| 5,269,809 A | 12/1993 | Hayhurst et al. |
| 5,320,115 A | 6/1994 | Kenna |
| 5,324,308 A | 6/1994 | Pierce |
| 5,350,399 A | 9/1994 | Erlebacher et al. |
| 5,370,661 A | 12/1994 | Branch |
| 5,413,585 A | 5/1995 | Pagedas |
| 5,462,542 A | 10/1995 | Alesi, Jr. |
| 5,464,407 A | 11/1995 | McGuire |
| 5,466,243 A | 11/1995 | Schmieding et al. |
| 5,500,000 A | 3/1996 | Feagin et al. |
| 5,522,844 A | 6/1996 | Johnson |
| 5,527,341 A | 6/1996 | Gogolewski et al. |
| 5,575,801 A | 11/1996 | Habermeyer et al. |
| 5,584,835 A | 12/1996 | Greenfield |
| 5,601,562 A | 2/1997 | Wolf et al. |
| 5,613,283 A | 3/1997 | Yusfan |
| 5,662,650 A | 9/1997 | Bailey et al. |
| 5,713,903 A | 2/1998 | Sander et al. |
| 5,720,753 A | 2/1998 | Sander et al. |
| 5,725,556 A | 3/1998 | Moser et al. |
| 5,797,932 A | 8/1998 | Min et al. |
| 5,810,854 A | 9/1998 | Beach |
| 5,814,051 A | 9/1998 | Wenstrom, Jr. |
| 5,814,071 A | 9/1998 | McDevitt et al. |
| 5,814,072 A | 9/1998 | Bonutti |
| 5,904,704 A | 5/1999 | Goble et al. |
| 5,906,631 A | 5/1999 | Imran |
| 5,938,686 A | 8/1999 | Benderev et al. |
| 5,948,000 A | 9/1999 | Larsen et al. |
| 6,013,083 A | 1/2000 | Bennett |
| 6,015,410 A | 1/2000 | Tormala et al. |
| 6,015,428 A | 1/2000 | Pagedas |
| 6,117,162 A | 9/2000 | Schmieding et al. |
| 6,206,886 B1 | 3/2001 | Bennett |
| 6,214,031 B1 | 4/2001 | Schmieding et al. |
| 6,241,748 B1 | 6/2001 | Adams |
| 6,241,749 B1 | 6/2001 | Rayhanabad |
| 6,293,961 B2 | 9/2001 | Schwartz et al. |
| 6,348,053 B1 | 2/2002 | Cachia |
| 6,491,714 B1 | 12/2002 | Bennett |
| 6,499,599 B1 | 12/2002 | Hopkins et al. |
| 6,533,802 B2 | 3/2003 | Bojarski et al. |
| 7,303,577 B1 | 12/2007 | Dean |
| 7,530,990 B2 | 5/2009 | Perriello et al. |
| 7,585,311 B2 | 9/2009 | Green et al. |
| 7,615,061 B2 | 11/2009 | White et al. |
| 7,637,926 B2 | 12/2009 | Foerster et al. |
| 7,658,750 B2 | 2/2010 | Li |
| 7,658,751 B2 | 2/2010 | Stone et al. |
| 7,674,274 B2 | 3/2010 | Foerster et al. |
| 7,682,374 B2 | 3/2010 | Foerster et al. |
| 7,686,838 B2 | 3/2010 | Wolf et al. |
| 7,695,494 B2 | 4/2010 | Foerster |
| 7,713,285 B1 | 5/2010 | Stone et al. |
| 8,814,904 B2 | 8/2014 | Bennett |
| 8,845,686 B2 | 9/2014 | Bennett |
| 2001/0025181 A1 | 9/2001 | Freedlan |
| 2002/0004668 A1 | 1/2002 | Bartlett |
| 2002/0004669 A1 | 1/2002 | Bartlett |
| 2002/0007196 A1 | 1/2002 | Bartlett |
| 2002/0161401 A1* | 10/2002 | Steiner ............... A61B 17/0401 606/232 |
| 2002/0173822 A1* | 11/2002 | Justin ................. A61B 17/0401 606/232 |
| 2005/0251209 A1 | 11/2005 | Saadat et al. |
| 2006/0058844 A1 | 3/2006 | White et al. |
| 2006/0106422 A1 | 5/2006 | Del Rio et al. |
| 2006/0106423 A1 | 5/2006 | Weisel et al. |
| 2007/0156151 A1 | 7/2007 | Guan et al. |
| 2007/0282375 A1 | 12/2007 | Hindrichs et al. |
| 2008/0082113 A1 | 4/2008 | Bishop et al. |
| 2008/0234731 A1 | 9/2008 | Leung et al. |
| 2009/0248071 A1 | 10/2009 | Saint et al. |
| 2009/0287227 A1 | 11/2009 | Newell et al. |
| 2010/0160963 A1 | 6/2010 | Fallin et al. |
| 2012/0101526 A1 | 4/2012 | Bennett |
| 2014/0364862 A1 | 12/2014 | Bennett |

FOREIGN PATENT DOCUMENTS

| | | |
|---|---|---|
| WO | WO 2014/055767 | 4/2014 |
| WO | WO 2014/164605 | 10/2014 |
| WO | WO2014164605 | 10/2014 |

\* cited by examiner

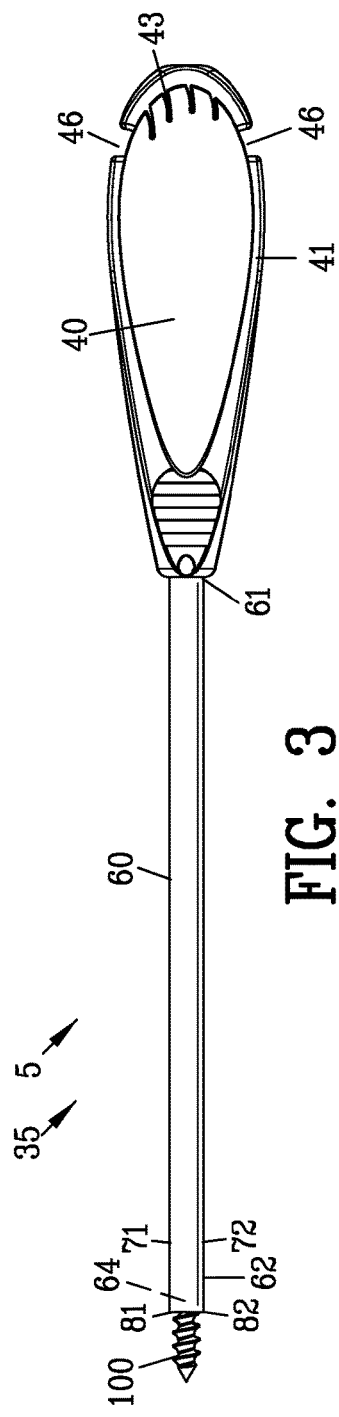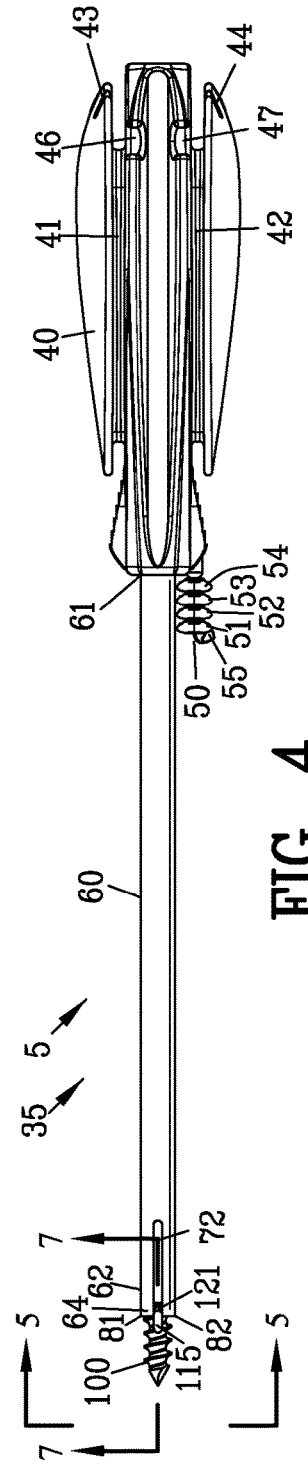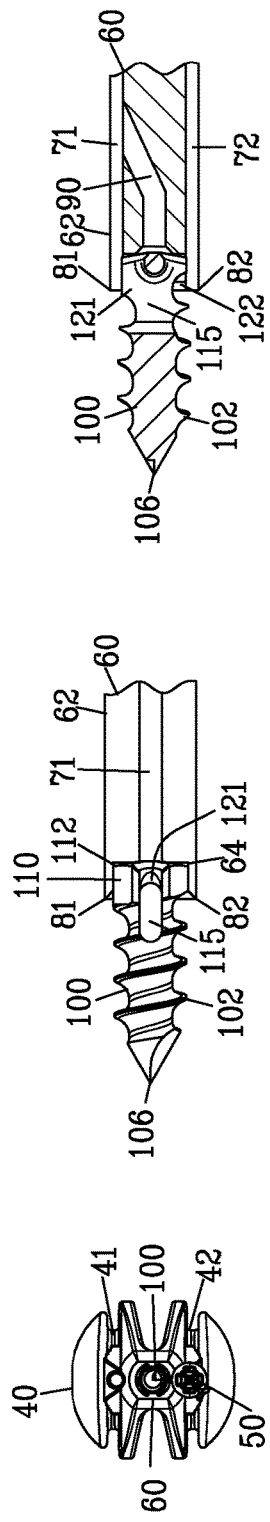

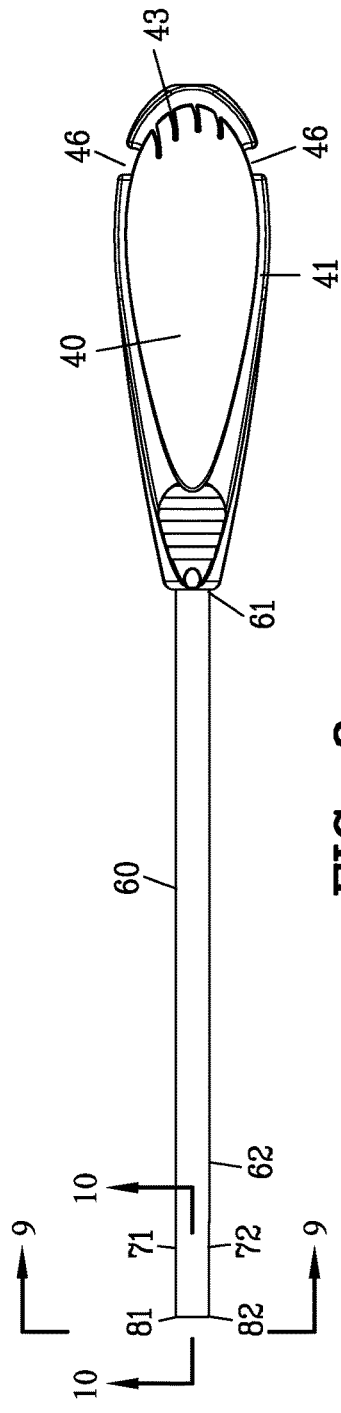
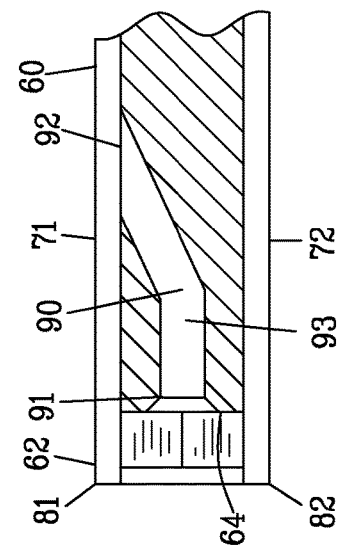
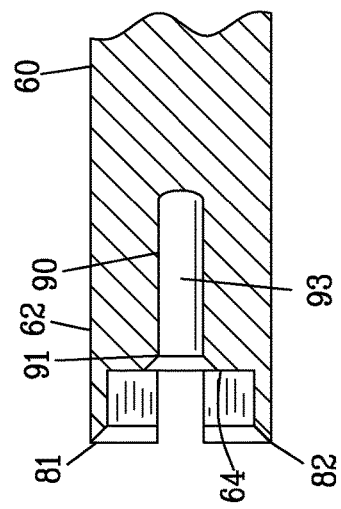
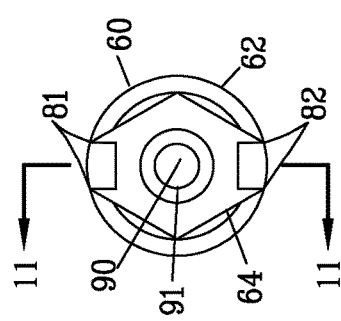
FIG. 8
FIG. 11
FIG. 10
FIG. 9

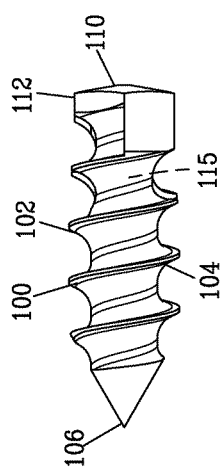
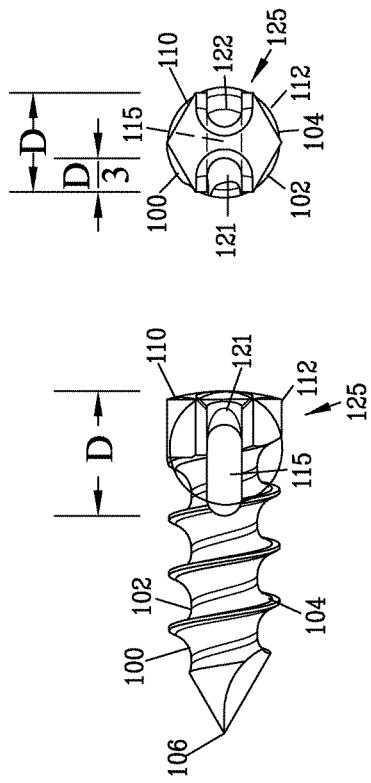
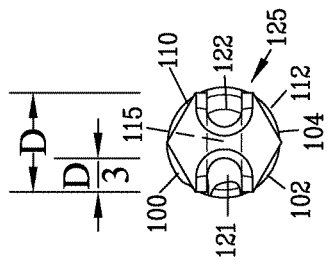
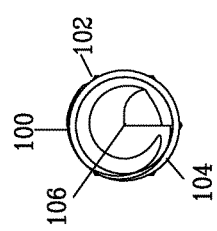
FIG. 12
FIG. 13
FIG. 14
FIG. 15

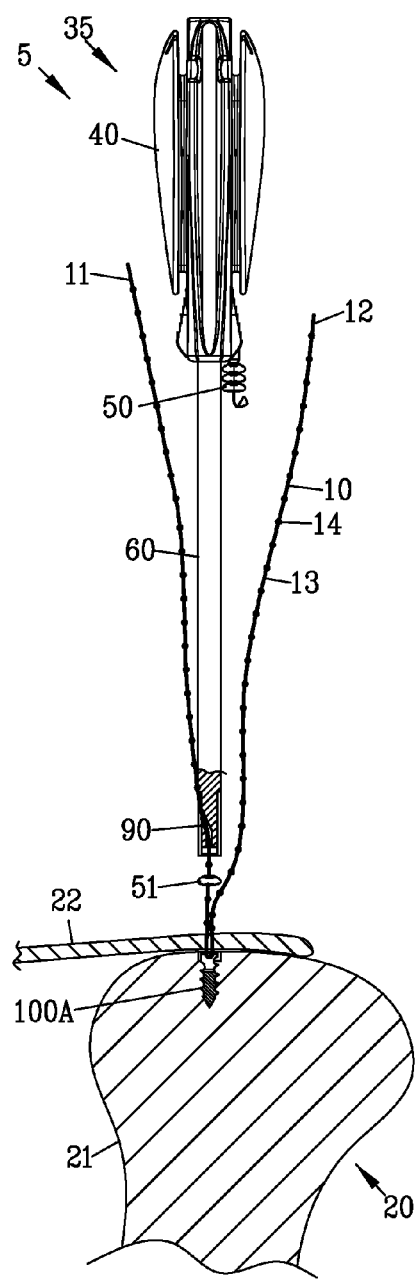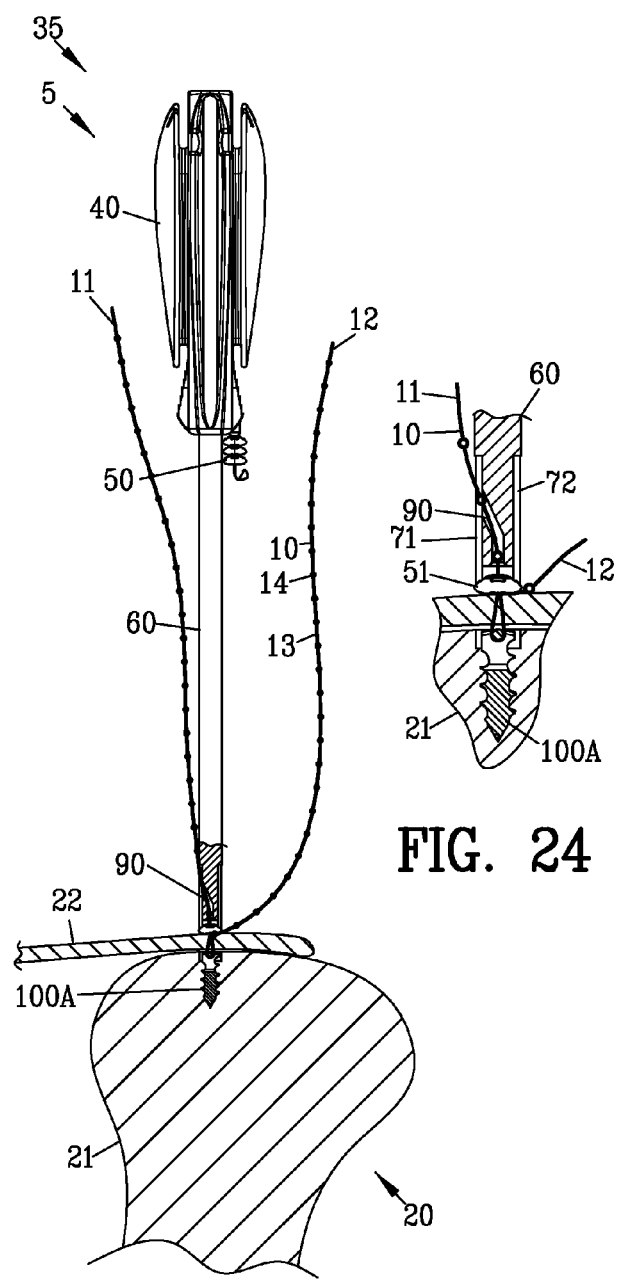
FIG. 22  FIG. 23  FIG. 24

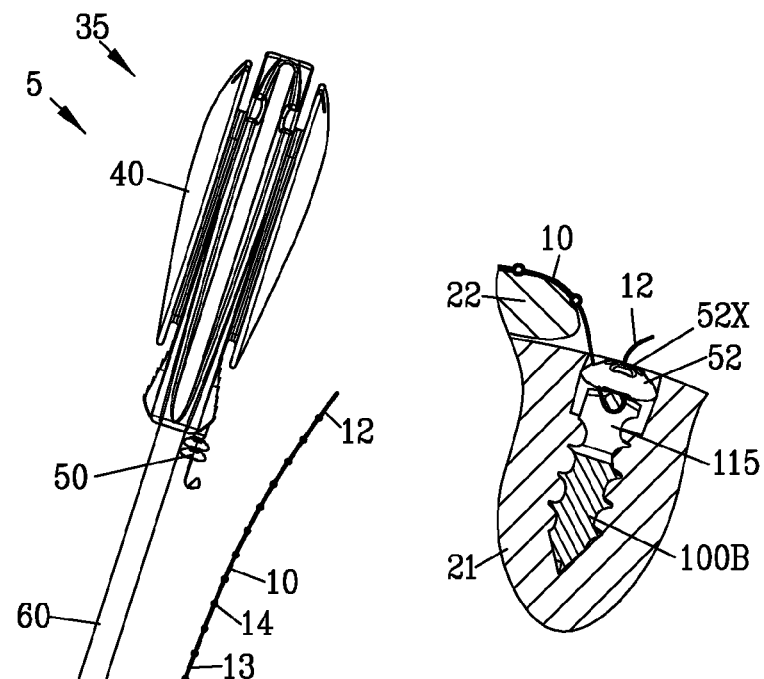
FIG. 35
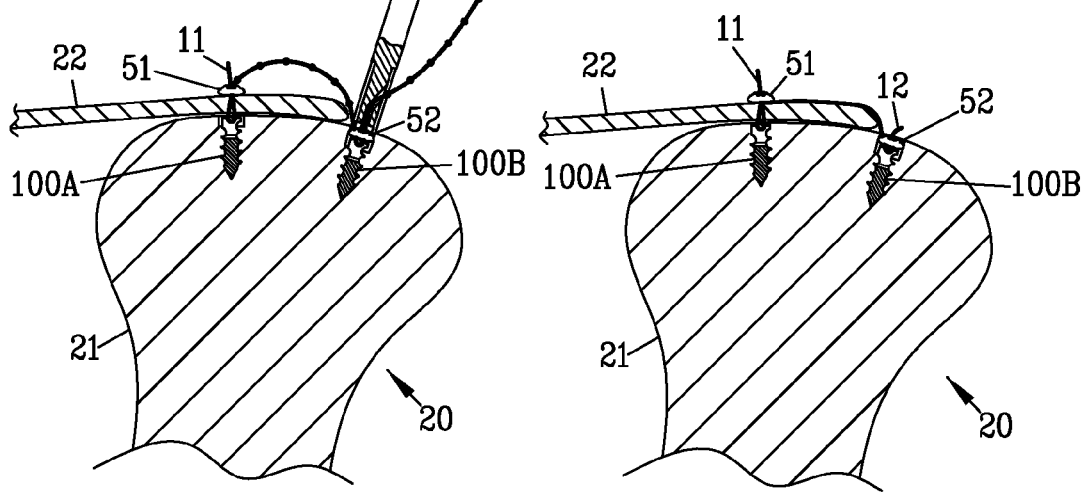
FIG. 33
FIG. 34

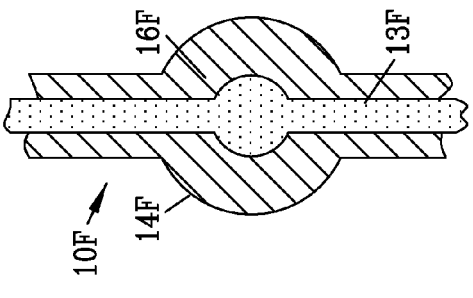
FIG. 44
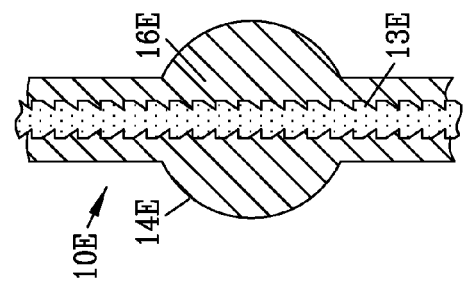
FIG. 45
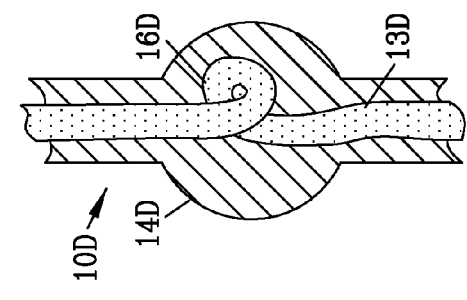
FIG. 46
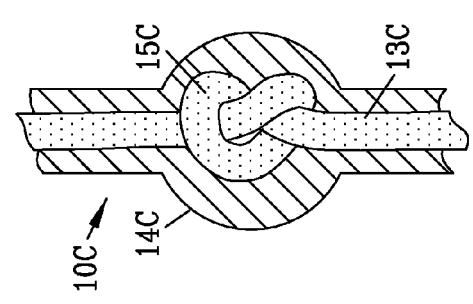
FIG. 47
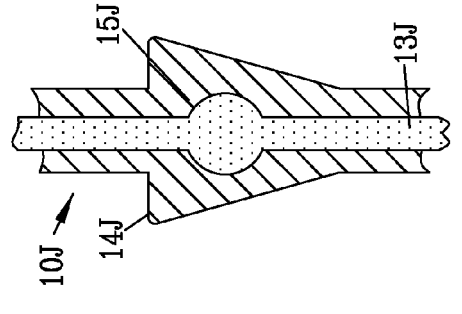
FIG. 48
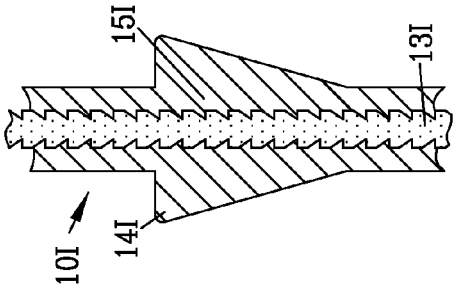
FIG. 49
FIG. 50
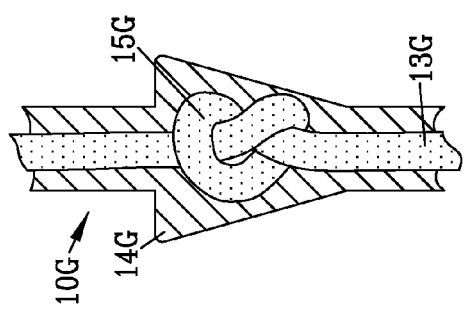
FIG. 51

FASTENER

CROSS-REFERENCE TO RELATED APPLICATIONS

This application is a Division of U.S application Ser. No. 14/203,846 filed Mar. 11, 2014. U.S application Ser. No. 14/203,846 filed Mar. 11, 2014 claims benefit of U.S. provisional application Ser. No. 61/778,350 filed 12 Mar. 2013. All subject matter set forth in U.S application Ser. No. 14/203,846 filed Mar. 11, 2014 and U.S. provisional application No. 61/778,350 filed 12 Mar. 2013 is hereby incorporated by reference into the present application as if fully set forth herein.

BACKGROUND OF THE INVENTION

Field of the Invention

This invention relates to surgery and more particularly to an apparatus and method for securing tissue comprising a novel screw anchor and rotational driver for securing a suture to a surgical button, a pledget or a capture.

Description of the Related Art

In recent years the use of captures have found increased use in the surgical art. Typically, a capture is used in association with a suture for securing an end of the suture without the need for tying a knot in the suture. The use of a capture has several advantages over the traditional tying of a suture. Firstly, a capture will secure a suture faster than tying a traditional knot. Secondly, a capture will generally yield more consistent holding strength relative to a traditional knot. Thirdly, a capture can be used in arthroscopic surgery where space limitation makes knot tying difficult for a surgeon.

The following prior art are examples of the development of captures and the like, including anchors, fasteners screws for the surgical art. These prior art examples may be used in various types of surgery including medical, veterinary and dental implants.

U.S. Pat. No. 4,898,156 to Gatturna, et al. discloses a suture anchor for anchoring one end of a conventional suture to bone comprising a coupling member, with at least one barb made of a resilient elastic material projecting from said coupling member, and structure for use in attaching one end of a suture to said suture anchor. The coupling member and the at least one barb are adapted to securely anchor one end of the suture in bone when the suture is attached to the attachment structure, so that the other end of the suture extending outside the bone can be used to attach objects to the bone. A novel application tool is also provided.

U.S. Pat. No. 5,733,307 to Dinsdale discloses a bone anchor with a suture trough for attaching bone to tissue using a suture. The bone anchor includes a threaded bone anchor body having a major diameter, a minor diameter, a tip, and a drive head. A suture trough is formed within the anchor body with a width greater than or equal to the diameter of the suture and a depth below the minor diameter greater than or equal to the diameter of the suture. A suture passageway connects the opposing portions of the suture trough. The suture seats within the suture trough during insertion of the bone anchor into the bone.

U.S. Pat. No. 5,370,661 to Branch discloses a method for attaching tissue to a bone, which includes the use of a filament member and a head member which engages the filament member and holds a tissue in place. Also provided is a device and method for repairing a break in tissue, which indicates the use of a filament member and at least one member which engages the filament member.

U.S. Pat. No. 5,413,585 to Pagedas discloses a self locking suture lock having a first suture thread opening in which the thread is secured before the surgical stitch and a cone shaped second stitch lock opening that is larger at the front side than at the back side, and designed to receive suture thread in only one direction, thereby locking it against withdrawal after the stitch to complete and lock it without the need for a surgical knot. A tongue in the second opening will allow passage through the cone shaped second opening from front side to back side but not allow passage from back to side to front side or pulling out of second opening once threaded. The front side of the self locking suture may be distinctively colored so that a surgeon will know which side of the suture lock will accept the suture thread. The first opening may take the form of a deformable slot, a pair of openings, or other forms. The tongue may engage the edge of the second opening, a slot, or other unidirectional lock structures.

U.S. Pat. No. 5,584,835 to Greenfield discloses a two-part device for suturing soft tissue to bone. The device employs a bone anchor which is installed in the bone and a suture anchor which is coupled to the soft tissue and then engaged with the bone anchor. The engagement of the suture anchor with the bone anchor is readily reversible so as to permit adjustments in the placement of the sutures. In the practice of the invention, no step is irreversible except the drilling of the bone hole that accepts the bone anchor. A special tool is described for facilitating the installation of a bone anchor having a round internal cross-section. The suture anchor can be installed with the application of only direct pressure, and can be disengaged by counterclockwise rotation, with the use of a disengagement tool, such as a screw driver. Sutures are threaded through apertures in the suture anchor, and the engagement of the sutures is enhanced by a friction fit between the suture and bone anchors.

U.S. Pat. No. 5,938,686 to Benderev, et al. discloses a bone anchor implantation device positioned over a bone, and a bone anchor installed in a bone.

U.S. Pat. No. 5,948,000 to Larsen, et al. discloses a system for suture anchor placement including an apparatus having a handle portion and an operating portion. The handle portion includes a spring, a needle park, and a member for releasably holding a length of the suture. The operating portion includes a sheath tube and a plunger rod slidably disposed within the bore of the sheath tube. The plunger rod is fixedly mounted at its proximal end to the handle. The suture anchor is releasably engaged to the distal end portion of the plunger rod. The sheath tube is mounted to the handle and movable with respect to the handle between a distal position and a proximal position, the sheath tube being resiliently biased to the distal position by the spring and movable to the proximal position in response to proximally directed force of sufficient magnitude applied to the distal end of the sheath tube. The sheath tube has a portion with an outer diameter greater than the diameter of the hole in the bone such that when the installation tool is pressed toward the bone, the sheath tube retracts into the handle and the suture anchor is advanced into a hole previously made in the bone. The suture, initially held in a taut configuration, is released in response to movement of the sheath tube to its proximal position.

U.S. Pat. No. 6,013,083 to Bennett discloses tom tissue such as a rotator cuff positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool. The deployment tool is passed through the inner cannula and drilled hole until the expandable wings clear the far end of the hole a sufficient distance to allow the wings to expand to a diameter larger than the diameter of the drilled hole. The deployment tool, inner cannula, drill guide, and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

U.S. Pat. No. 6,015,410 to Tormala, et al. discloses a bioabsorbable surgical implant for use in supporting soft tissue in a superior position in the body. The surgical implant includes a shaft that connects the implant to a bone or hard tissue and a head secured to the shaft. The head of the implant has a concave lower surface so that a suture (or sutures) can easily be wound around the shaft below the head and locked to this position by tightening the head against bone or hard tissue and by pushing or turning the shaft into the bone or hard tissue. The connected shaft and head are formed from a resorbable polymer, copolymer, polymer alloy or composite, which maintains a specified strength for a period of time at least equal to a healing period for the patient. Thereafter, the surgical implant is substantially resorbed by the body over a period of time needed for healing. The surgical implant is particularly adapted for use in endoscopic face and/or brow lift surgery and other endoscopic cosmetic, plastic and reconstructive surgical procedures, where sutures are applied for tissue lifting.

U.S. Pat. No. 6,117,162 to Schmieding, et al. discloses a corkscrew suture anchor having a continuous thread spiralling around a tapering central core. At the distal end, the suture anchor terminates in a rounded point. At the proximal end of the suture anchor is an eye for receiving suture. The suture anchor has a large thread surface per turn of thread. Anti-backout ridges can be formed on the front and/or back faces of the threads. A driver for the suture anchor is provided, the driver including a shaft having a central axis, a length, a distal end, and a proximal end. The shaft is provided at its distal end with an opening aligned with the central axis of the shaft, for receiving the hexagonal proximal end of the suture anchor. One or more sutures threaded through the suture eye are threaded through the hollow tubular shaft. The suture is pulled into and captured by V-shaped notches on the proximal end of the handle to hold the suture anchor in place on the distal end of the driver under the tension of the captured sutures.

U.S. Pat. No. 6,206,886 to Bennett discloses torn tissue such as a rotator cuff positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool. The deployment tool is passed through the inner cannula and drilled hole until the expandable wings clear the far end of the hole a sufficient distance to allow the wings to expand to a diameter larger than the diameter of the drilled hole. The deployment tool, inner cannula, drill guide, and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

U.S. Pat. No. 6,214,031 to Schmieding, et al. discloses a corkscrew suture anchor having a continuous thread spiralling around a tapering central core. At the distal end, the suture anchor terminates in a rounded point. At the proximal end of the suture anchor is an eye for receiving suture. The suture anchor has a large thread surface per turn of thread. Anti-backout ridges can be formed on the front and/or back faces of the threads. A driver for the suture anchor is provided, the driver including a shaft having a central axis, a length, a distal end, and a proximal end. The shaft is provided at its distal end with an opening aligned with the central axis of the shaft, for receiving the hexagonal proximal end of the suture anchor. One or more sutures threaded through the suture eye are threaded through the hollow tubular shaft. The suture is pulled into and captured by V-shaped notches on the proximal end of the handle to hold the suture anchor in place on the distal end of the driver under the tension of the captured sutures.

U.S. Pat. No. 6,293,961 to Schwartz, et al. discloses a device for locking a suture in place without the need for tying knots once the suture is placed within tissue. The device comprises an anchor having a front section and a rear section, a cannula extending through the front and rear sections through which the suture extends, and a bead positioned adjacent an end of the suture for locking the suture within the cannula.

U.S. Pat. No. 6,491,714 to Bennett discloses a surgical apparatus for anchoring and reattachment of torn tissue such as a rotator cuff against on the outer or exterior surface of a tissue substrate. The invention includes a tissue substrate anchor such as that having expandable wings. an elongated suture member securable at its proximal end to the tissue substrate anchor, and a torn tissue retainer lockingly attachable along the length of the suture member by mating interlocking structure therebetween. Tension is applied to the free distal end of the suture member while the tissue retainer is non-reversibly moved longitudinally along on the suture member to secure the torn tissue against the tissue substrate outer surface. A separate torn tissue gripping member may also be provided for broadened and enhanced torn tissue securement against the tissue substrate. In another embodiment, the tissue anchor is formed as a unit with the suture member enabling additional forms of tissue repair such as the closure of an internal meniscus tear or separation.

U.S. Pat. No. 6,533,802 to Bojarski, et al. discloses a method of securing a tissue graft within a bone passage including providing a graft fixation member comprising a closed-loop having a pair of opposing loop sections and capturing a first loop section of the closed-loop within the fixation member. An opposing second loop section of the closed loop is passed through an opening in the tissue graft, and the second loop section of the closed loop is secured to the fixation member.

U.S. Pat. No. 7,303,577 to Dean discloses a method, system and apparatus for augmenting the surgical repair of soft tissue injuries, in which a first end of a bridge member attaches to a first portion of healthy tissue, and a second end of the bridge member attaches to a second portion of healthy tissue. The bridge member (or bridge members) used to augment the soft tissue repair may be interconnected or function independently. Flexibility and elasticity of the bridge member are determined by the situation and may be altered to improve healing. The device may be used in arthroscopic procedures, and may be manufactured in a variety of lengths, or may be manufactured one length and be cut to the desired length, or otherwise altered to provide an optimal length of the bridge member.

U.S. Pat. No. 7,530,990 to Perriello, et al. discloses a method of securing a tissue graft within a bone passage including providing a graft fixation member comprising a closed double-loop having a pair of differently sized loop sections and capturing both sections of the closed-loop within the fixation member. The longer loop section is passed through an opening in the tissue graft then is passed through the smaller loop and thrown over the fixation member to form a knot.

U.S. Pat. No. 7,585,311 to Green, et al. discloses a method and device for securing soft tissue to a rigid material such as bone. A bone anchor is described that comprises a base and a top such that suture material may be compressed between surfaces on the base and top to secure the suture to the anchor. Also described is an inserter that can be used to insert the bone anchor into bone and move the anchor top relative to the anchor base to clamp suture material there between. Also described is a soft-tissue and bone piercing anchor and associated inserter. Methods are described that allow use of the bone anchors to provide multiple lengths of suture material to compress a large area of soft tissue against bone.

U.S. Pat. No. 7,615,061 to White, et al. discloses a suture-loading system, method and apparatus for loading a suture onto a bone anchor. The system comprising: a bone anchor comprising a suture leg-anchoring structure and a plurality of body holes on the anchor; a suture comprising a standing end portion and a working end portion; a standing end trackway to guide the standing end portion of the suture through the suture leg-anchoring structure; and a working end trackway to guide the working end portion of the suture through the body holes in the anchor.

U.S. Pat. No. 7,637,926 to Foerster, et al. discloses an innovative bone anchor and method for securing soft tissue, such as tendons, to bone, which permit a suture attachment that lies entirely beneath the cortical bone surface. Advantageously, the suturing material between the soft tissue and the bone anchor is secured without the need for tying a knot. The suture attachment to the bone anchor involves the looping of a length of suture around a pulley within the bone anchor, tightening the suture and attached soft tissue, and clamping the suture within the bone anchor. The bone anchor may be a tubular body having a lumen containing a plurality of suture-locking elements that clamp the suture therein. The locking elements may be thin and C-shaped. One or more locking plugs attached to separable actuation rods displace axially within the lumen and act on the locking elements to displace them radially. A generally uniform passage through the locking elements in their first positions converts to a smaller irregular passage after the locking plug displaces the elements to their second positions, thus effectively clamping the suture. The bone anchor further may include locking structure for securing itself within a bone cavity.

U.S. Pat. No. 7,658,750 to Li discloses a suture anchoring system and method including a plurality of anchor members interconnected to form an anchor assembly with a suture extending therefrom. The anchor assembly has an insertion configuration wherein the anchor members are aligned in a substantially linear arrangement for delivery through an aperture in bodily tissue and an expanded configuration wherein the anchor members are transitioned to a non-linear arrangement to prevent passage of the anchor assembly back through the aperture.

U.S. Pat. No. 7,658,751 to Stone, et al. discloses a suture construction and method for forming a suture construction. The construction utilizes a suture having an enlarged central body portion defining a longitudinal passage. First and second ends of the suture are passed through first and second apertures associated with the longitudinal passage to form a pair of loops. Portions of the suture lay parallel to each other within the suture. Application of tension onto the suture construction causes constriction of the longitudinal passage, thus preventing relative motions of the captured portions of the suture.

U.S. Pat. No. 7,662,157 B2 to Ahmad discloses a bone anchor including a screw portion configured to penetrate a bone. The screw portion includes a retention thread extending at least part of a length of the screw portion and a tip at a first end of the screw portion. The bone anchor includes a protrusion adjacent a second end of the screw portion. The second end is opposite the first end of the screw portion. The protrusion comprises a plurality of external sides forming a shape and a rounded interior surface enclosing a protrusion recess. The rounded interior surface includes a recess thread configured to retain a component at least partially in the protrusion recess. The protrusion has a maximum width that is less than a maximum diameter of the screw portion such that a shoulder is formed where the protrusion meets the second end of the screw portion.

U.S. Pat. No. 7,674,274 to Forester, et al. discloses a bone anchor device for attaching connective tissue to bone comprising a disk adapted for insertion into a portion of bone to which the connective tissue is to be attached. The disk is movable between a bent orientation for presenting a smaller cross-section and an expanded orientation for presenting a larger cross-section. The bent orientation is utilized for inserting the disk through a small hole into a region of cancellous bone beneath the cortical bone layer, after which the disk is actuated to its expanded orientation so that it will be permanently anchored in the cancellous bone, as it will be too large to return proximally through the hole in the cortical bone layer. Two embodiments are disclosed. In a first embodiment, the disk is initially formed in the expanded orientation, of spring steel. In a second embodiment, the disk is initially formed in the bent orientation, and spring steel is not required.

U.S. Pat. No. 7,686,838 to Wolf, et al. discloses a surgical anchor device for the repair of a torn ligament or tendon, primarily the anterior cruciate ligament in the knee. The device is used to affix the ligament within a femoral bone tunnel in the distal portion of the femur from the intra-articular surface. The device provides a pulley for a suture, wherein a free end of the suture may be pulled away from the device to draw the suture attached to the ligament graft within the femoral bone tunnel securing the ligament graft within the bone tunnel. Installation of the device is provided by insertion of the device through a tibial hole, through the femoral tunnel out of the lateral femoral cortex, pulling the attached sutures simultaneously to flatten the device against the lateral femoral cortex, attaching one end of the suture to the ligament graft and pulling the other end of the suture until the graft is situated properly within the femoral bone tunnel and tying the free end of the suture to retain the graft within the femoral bone tunnel.

U.S. Pat. No. 7,695,494 to Foerster discloses a device for attaching connective tissue to bone. The device has a longitudinal axis and comprises an annular toggle member and a body member disposed distally of the toggle member, such that there is an axial space between the toggle member and the body member. The toggle member is movable between an undeployed position wherein the toggle member has a smaller profile in a direction transverse to the axis and a deployed position wherein the toggle member has a larger profile in the direction transverse to the axis. When installed in a desired procedural site, in suitable bone, suturing material extends axially through a center aperture in the annular toggle member, without being secured to or contacting the toggle member. This approach permits a suture attachment which lies entirely beneath the cortical bone surface, and which further permit the attachment of suture to the bone anchor without the necessity for tying knots, which is particularly arduous and technically demanding in the case of arthroscopic procedures.

U.S. Pat. No. 7,713,285 to Stone, et al. discloses a suture anchor for anchoring a suture in the selected portion of an anatomical portion for fixing a suture thereto. The suture anchor includes an anatomical engaging portion and a suture engaging portion wherein both the anatomical engaging portion and a suture engaging portion are adapted to be substantially disposed below an exterior of the anatomical portion after implantation. Suture eyelets are provided in the suture engaging section and a suture passage is formed to interconnect the eyelets to allow a suture to be easily threaded in the suture engaging section from the first eyelet to the second eyelet.

United States Patent Application 2002/0004668 to Bartlett discloses a suture anchor comprising a generally quadrilaterally shaped body having a bore-abutting surface with a leading gripping edge at one end of the bore-abutting surface, a trailing gripping edge at the other end, and a closing surface having an arcuate portion and a linear portion engaging the leading and trailing gripping edges, respectively, generally opposite the bore-abutting surface. The body further defines a suture bore extending transversely therethrough and an inserter bore adapted to receive an insertion tool. A suture engages the suture anchor through the bore and is adapted to engage bodily tissue to be secured to the bone. Also provided are a knotless suture anchor configuration, an associated insertion tool, and a suture anchor kit, as well as a method of implanting a suture anchor in a bore in a bone.

United States Patent Application 2002/0004669 to Bartlett discloses a suture anchor comprising a generally quadrilaterally shaped body having a bore-abutting surface with a leading gripping edge at one end of the bore-abutting surface, a trailing gripping edge at the other end, and a closing surface having an arcuate portion and a linear portion engaging the leading and trailing gripping edges, respectively, generally opposite the bore-abutting surface. The body further defines a suture bore extending transversely therethrough and an inserter bore adapted to receive an insertion tool. A suture engages the suture anchor through the bore and is adapted to engage bodily tissue to be secured to the bone. Also provided are a knotless suture anchor configuration, an associated insertion tool, and a suture anchor kit, as well as a method of implanting a suture anchor in a bore in a bone.

United States Patent Application 2002/0007196 to Bartlett discloses a suture anchor comprising a generally quadrilaterally shaped body having a bore-abutting surface with a leading gripping edge at one end of the bore-abutting surface, a trailing gripping edge at the other end, and a closing surface having an arcuate portion and a linear portion engaging the leading and trailing gripping edges, respectively, generally opposite the bore-abutting surface. The body further defines a suture bore extending transversely therethrough and an inserter bore adapted to receive an insertion tool. A suture engages the suture anchor through the bore and is adapted to engage bodily tissue to be secured to the bone. Also provided are a knotless suture anchor configuration, an associated insertion tool, and a suture anchor kit, as well as a method of implanting a suture anchor in a bore in a bone.

United States Patent Application 2006/0058844 to White, et al. discloses an internal tissue puncture closure method and apparatus providing a locking device for compressing and holding an external component such as a collagen sponge at a puncture situs. The locking device facilitates compression of the external component in a first direction, but prevents or locks against retraction.

United States Patent Application 2006/0106422 to Del Rio, et al. discloses suture tying in a medical procedure including the use of an anchor that includes a suture locking device. The device includes a sliding pin guided by axial side slots formed in the locking device that forces the suture where the two ends thereof are inserted into the interior of the suture locking mechanism to drive the captured suture and pin to fit into a recess on the top of the suture locking mechanism such that the top of the pin binds the suture against the upper inner surface of the recess. The recess can be serrated to enhance the locking capability and the pin is polygonal shaped to provide side surfaces that run parallel to the wall of the recess to assure that the side portion of the pin does not fracture the suture and cause it to weaken. The locking of the suture is automatic upon the deployment of the anchor which actuates the pin into the locking position, thus eliminating the necessity of manually knotting the suture and improving the cinching of the tissue to the bone. The suture locking mechanism is usable for attaching tissue to the bone, tying tissue to tissue and the like. The disclosure also includes the method of deploying the combined anchor and suture locking device in a medical procedure.

United States Patent Application 2007/015651 to Guan, et al. discloses an expanding plug for tendon fixation featuring a two-part system in which an expansion pin fits inside a fixation sleeve. The fixation sleeve is configured to expand diametrically to achieve interference fixation of a graft tendon inside of a bone tunnel. Fixation sleeve expansion is urged by a two-step engagement of the expansion pin. The tendon graft is assembled to the expanding bolt and situated within a bone tunnel. Passing suture is used to pull a joint-line end of the expansion pin into the tunnel to partially expand the fixation sleeve at the joint-line end. Pulling a graft end of the expansion pin toward the joint line expands the fixation sleeve to place the expanding plug in the fully deployed configuration.

United States Patent Application 2007/028375 to Hindrichs, et al. discloses an implant structure for use in pulling two soft body tissue areas closer together in a patient (e.g., two points along or adjacent to the patient's mitral valve annulus) including at least two tissue anchor structures that are respectively implantable into the two tissue areas. A tether structure links the two tissue anchors and can be shortened and held in that condition by a cinch structure. Bracing structures are used between the anchors and the tether to help keep the longitudinal axes of the anchors transverse to the tether axis even when the tether is under tension. The tether may be sheathed in a cushioning sleeve to help protect adjacent tissue from erosion by the tether.

United States Patent Application 2008/0082113 to Bishop, et al. discloses embodiments of apparatus and methods for tissue lifting, or for correcting a ptosis condition caused by tissue stretching. In some embodiments a tissue is supported by a support member. In some embodiments, tension is applied to a support member through at least one suspension member. The described embodiments provide examples of methods and apparatus effective for use in lifting or otherwise applying tension to various tissues, including tissues of the breast, buttock, thigh, arm, abdomen, neck and face.

United States Patent Application 2008/0234731 to Leung, et al. discloses a suture anchor for approximating tissue to bone or other tissue. The suture anchor comprises an anchor member to fixedly engage the bone for securing the anchor member relative to the bone. A plurality of sutures are mounted to the proximal end of the anchor member so that the sutures extend outwardly from the anchor member. Each suture has a sharp pointed distal end for penetrating the tissue and a plurality of barbs extending from the periphery and disposed along the length of the body of the suture. The barbs permit movement of the sutures through the tissue in a direction of movement of the pointed end and prevent movement of the sutures relative to the tissue in a direction opposite the direction of movement of the pointed end. At least one pointed distal end of at least one suture comprises a needle.

United States Patent Application 2009/0248071 to Saint, et al. discloses methods and apparatus for use in supporting tissue in a patient's body. In some embodiments, the patient's breast is supported. In some embodiments, the methods provide ways of supporting and adjusting tissue, and the apparatus includes components and embodiments for supporting and adjusting the tissue. Some embodiments include a supporting device, having a first portion, a second portion, and a support member positioned between the first portion and second portion. Some embodiments include advancing the first portion of the supporting device into the body to a first location in the body; advancing the second portion of the supporting device into the body to a second location in the body; securing the first portion of the supporting device at the first location; and shifting soft tissue in the body with the support member.

United States Patent Application 2009/0287227 to Newell, et al. discloses methods, systems, devices and assemblies for treating a patient by: making an incision or puncture though the patient's skin over the abdominal cavity. An initial tract is established through an opening formed by the incision or puncture. An instrument is advanced through the tract; contacting a distal end portion of the instrument against an inner surface of the abdominal cavity, and driving at least one stitching needle through the inner surface of the abdominal cavity. The driving is continued until the at least one stitching needle exits the inner surface of the abdominal cavity. A suture anchor is carried by each of the at least one stitching needle to a suture anchor at an exit location, respectively. Tension is applied to each of the sutures.

United States Patent Application 2010/0101526 to Bennett discloses a surgical suture system, suture, and tissue engaging member for tissue repair and reattachment of torn tissue to a tissue substrate, medical prosthesis or medical implant. The system includes the elongated flexible suture member having a plurality of longitudinally spaced protuberances along a length thereof and one or a plurality of the tissue engaging members each of which include two closely spaced apart locking apertures sized and configured to receive one of the suture members passed therethrough or a unique single locking aperture to allow longitudinal tensioning and/or restraining movement of the suture member in only one direction through the locking apertures for suture member tightening.

United States Patent Application 2010/0160963 to Fallin, et al. discloses a system for attaching soft tissue to bone including an anchor, a suture, and a tissue retainer. The anchor may have a threaded tip that engages the bone, and a suture retention portion with passageways arranged such that each of first and second anchor portions of the suture can be drawn through the passageways along only a single direction. The tissue retainer has passageways through which the suture can freely move in either direction. Thus, the anchor and the tissue retainer may be attached to bone and tissue, respectively, and the suture may be drawn to substantially irreversibly draw the bone and tissue together. In alternative embodiments, an anchor may receive only one portion of suture and/or one suture end may be affixed to the anchor. The anchor may alternatively permit free motion of the suture, while the tissue retainer permits passage of the suture along only one direction.

United States Patent Application 2012/0101524 to Bennett discloses a surgical suture system for tissue repair and reattachment of torn tissue to a tissue substrate, medical prosthesis or medical implant. The system includes an elongated flexible suture member having a plurality of longitudinally spaced protuberances along a length thereof and a plurality of tissue engaging members each including two spaced apart locking apertures sized to receive the suture member passed therethrough to allow longitudinal movement of the suture member in only one direction through the locking apertures for suture member tightening.

United States Patent Application 2013/0090686 to Covidien discloses barbed surgical sutures are provided which include an elongated body and a plurality of barbs extending therefrom. A bioactive agent is disposed within barb angles formed between the barbs and the elongated body. The barbs may be made from a shape memory polymer having a permanent shape which may be deformed to a temporary shape, such that barbs of the suture extend at different barb angles in the different shape configurations. The barb angles of the permanent shape may be greater than the barb angles of the temporary shape, thereby exposing and/or releasing a bioactive agent after placement in tissue.

Although the forgoing prior art has contributed to the surgical art, none of these have provided a new system for securing sutures to a tissue or a bone suitable for use in general as well as arthroscopic, endoscopic, laparoscopic or minimally invasive surgery.

Therefore, it is an object of the invention to provide an improved hand tool comprising a rotation driver for rotationally inserting a screw within a bone.

Another object of this invention is to provide a novel screw suitable for use with the rotation driver for completely embedding the screw into the bone while permitting a suture to be threaded through a transverse aperture in the screw.

Another object of this invention is to provide a rotation driver for facilitating the insertion and engagement of a capture with one of a series of protuberance formed along a length of a suture.

Another object of this invention is to provide a method for forming a series of protuberance along a length of a suture.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with accompanying drawings.

SUMMARY OF THE INVENTION

The present invention is defined by the appended claims with specific embodiments being shown in the attached drawings. For the purpose of summarizing the invention, the first embodiment of the invention relates to an improved hand tool for rotationally inserting a screw within a bone. The hand tool comprises a rotational driver having a handle supporting a shaft extending from a proximal end to a distal end. A socket is defined in the distal end of the shaft for receiving a head of the screw for rotationally inserting the screw within the bone. A first and a second slot is located in the socket defining a first and a second cutting edge for cutting the bone upon rotation of the rotational driver to simultaneously insert the screw and countersink the head of the screw within the bone and also allow suture from as receiving screw to pass out from screw and along driver shaft without engaging sharp countersinking edges of driver.

A second embodiment of the invention relates to an improved fastener for insertion into a living tissue by a rotational driver. The fastener comprises a screw body extending between a screw tip and a screw head. The screw head defines a socket shape in an outer periphery of the screw head for enabling the rotational driver to rotationally insert the screw body into the living tissue. A transverse aperture extends through the screw body below the screw head. A first and a second channel is defined in opposed sides of the screw head and communicates with the transverse aperture for enabling a suture to extend through the first and second channels and the transverse aperture while the screw body is inserted into the living tissue by the rotational driver. The first and second channels and the transverse aperture are dimensioned for enabling the suture to be moved through the first and second channels and the transverse aperture when the screw body is totally embedded into the living tissue and allows for the shuttling of a suture through the embedded screw.

A third embodiment of the invention relates to a method of securing a tissue to a bone with a suture. The suture has a series of protuberances spaced apart along a length thereof. The method comprises the steps of rotating a driver for driving a screw into the bone with the suture extending through the transverse aperture in the screw. A first end of the suture is passed through a central aperture in the driver and is threaded through a central aperture in a capture. The capture is pushed with the driver along the suture to lockingly engage the capture with one of the series of protuberances for securing the first end of the suture. A second end of the suture is secured for securing the tissue to the bone.

A fourth embodiment of the invention relates to a method for forming a protuberance on a suture comprising the steps of placing a suture to extend through a mold cavity. An adhesive is inserted into the mold cavity. The adhesive is permitted to cure in the mold. The suture and the adhered protuberance is removed from the mold. Preferably, each of the mold cavities has a leading edge shape defined for cooperation with the entrance aperture contour of the capture and a trailing edge shape defined for cooperation with the reverse aperture contour of the capture. Other methods include a process that requires the application of a melted substance-requiring substantial temperatures to place material onto a suture which can damage the suture itself, this technique includes the application of an adhesive that sets at ambient temperature or some other method that do not affect the suture.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 3 is a top view of the rotational driver and screw of FIGS. 1 and 2;

FIG. 4 is a side view of FIG. 3;

FIG. 5 is an enlarged view along line 5-5 in FIG. 4;

FIG. 6 is an enlarged view of a portion of FIG. 4;

FIG. 7 is an enlarged sectional view along line 7-7 in FIG. 4;

FIG. 8 is a top view similar to FIG. 3 illustrating the rotational driver;

FIG. 9 is an enlarged view along line 9-9 in FIG. 8;

FIG. 10 is a sectional view along line 10-10 in FIG. 8;

FIG. 11 is a sectional view along line 11-11 in FIG. 9;

FIG. 12 is an enlarged side view of the improved fastener of the present invention shown in FIGS. 1-7;

FIG. 13 is a top view of the screw of FIG. 12;

FIG. 14 is a left end view of the screw of FIG. 12 illustrating the tip of the screw;

FIG. 15 is a right end view of the screw of FIG. 12 illustrating the head of the screw;

FIG. 22 illustrates the step of passing the first end of the suture through a central aperture in the driver;

FIG. 23 illustrates the step of pushing the capture with the driver along the suture to lockingly engage the capture with one of the series of protuberances for securing the first end of the suture;

FIG. 24 is an enlarged view of a portion of FIG. 23;

FIG. 33 illustrates the step of pushing the second capture with the driver along the suture to lockingly engage the second capture with one of the series of protuberances for securing the second end of the suture;

FIG. 34 illustrates the second capture lockingly engaged with one of the series of protuberances the suture;

FIG. 35 is an enlarged view of a portion of FIG. 34 showing the capture flush in the bone;

FIGS. 44-51 illustrate variations within the longitudinal suture or suture redundancies which allow the adhesive to hold more securely to the suture and prevent the protuberances from sliding along the length of the suture during a tensile load;

FIG. 44 is a sectional view of a third example of a protuberance formed on a suture;

FIG. 45 is a sectional view of a fourth example of a protuberance formed on a suture;

FIG. 46 is a sectional view of a fifth example of a protuberance formed on a suture;

FIG. 47 is a sectional view of a sixth example of a protuberance formed on a suture;

FIG. 48 is a sectional view of a seventh example of a protuberance formed on a suture;

FIG. 49 is a sectional view of a eighth third example of a protuberance formed on a suture;

FIG. 50 is a sectional view of a ninth example of a protuberance formed on a suture;

FIG. 51 is a sectional view of a tenth example of a protuberance formed on a suture;

Similar reference characters refer to similar parts throughout the several Figures of the drawings.

DETAILED DISCUSSION

Figure 1:
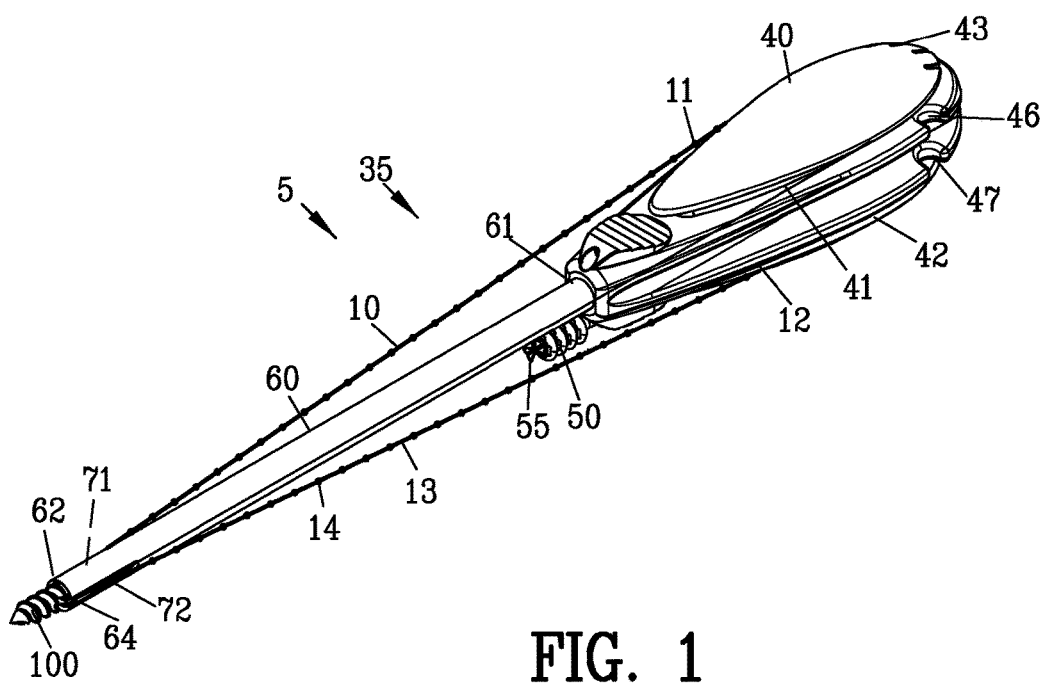
FIG. 1 is a top isometric view of a rotational driver and a screw incorporating the present invention.
Figure 2:
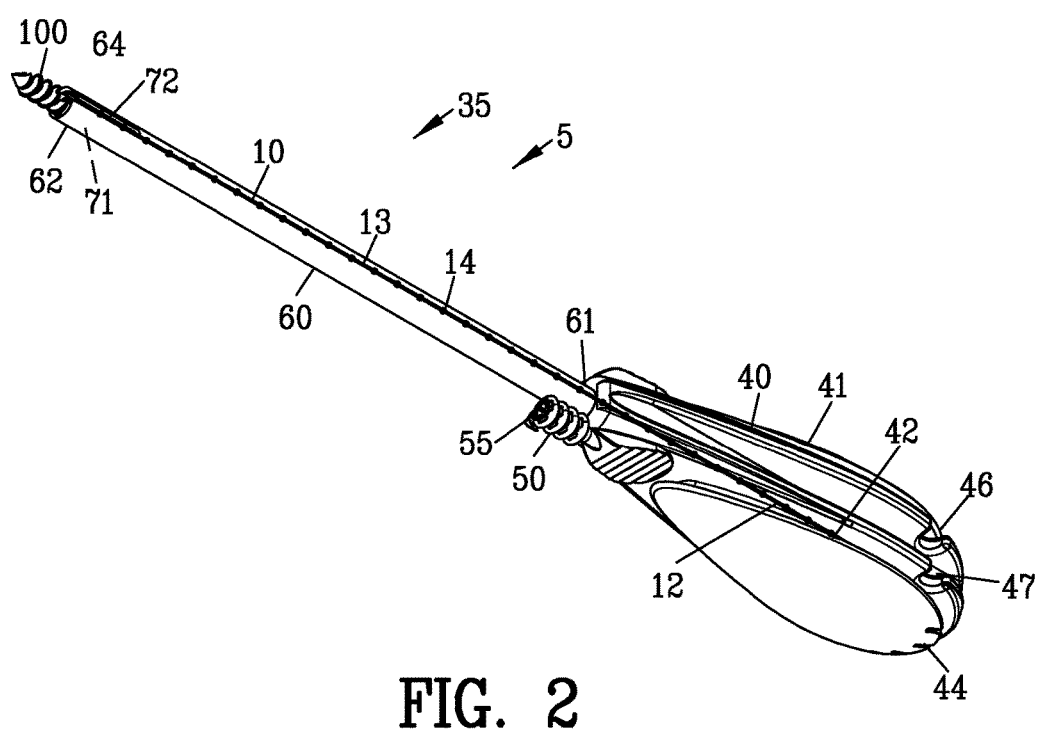
FIG. 2 is a bottom isometric view of FIG. 1.

FIGS. 1-7 are various views of an apparatus 5 for securing a suture 10 to living tissue 20 shown in FIGS. 21-35. In this example, the suture 10 has a flexible component 13 and a series of protuberances 14 spaced apart and along a length of the flexible component 13. The flexible component 13 may be a monofilament or may be a braded flexible component 13. The protuberances 14 may be formed or molded along the length of the flexible component 13 or may be knots tied along the length of the flexible component 13.

The apparatus 5 comprises an improved hand tool shown as a rotational driver 35 having a handle 40 supporting a shaft 60. The handle 40 includes a first and a second suture retainer 41 and 42 located on opposed sides of the handle 40. A first and a second jam cleat 43 and 44 cooperate with the first and second suture retainers 41 and 42 for temporarily retaining at least one suture 10. In this embodiment, the first retainer 41 and first jam cleat 43 retains a first end 11 of the suture 10 whereas the second retainer 42 and the second jam cleat 44 temporarily retains a second end 12 of the suture 10. A first and second pass through 46 and 47 are defined in the first and second suture retainers 41 and 42 for passing a suture between opposed sides of the handle 10. As will be described in greater detail hereinafter, the suture 10 extends through a screw 100 for enabling the rotational driver 35 to rotationally insert a screw 100 into the living tissue 20 while the suture extends through the screw 100.

As best shown in FIG. 4, a capture magazine 50 is located on the handle 40 in proximity to the juncture of the handle 40 and the shaft 60. In this embodiment, the capture magazine 50 is shown storing captures 51-54 threaded onto a resilient wire loop 55. The resilient wire loop 55 extends through capture orifices within each of the captures 51-54. As will be described in greater detail here and after, the resilient wire loop 55 facilitates threading of the suture 10 through the capture orifice in the capture 51.

The shaft 60 extends from a proximal end 61 adjacent to the handle 42 a distal end 62. A socket 64 is defined in the distal end 62 of the shaft 60 for receiving the screw 100. Preferably, the screw 100 is retained in the socket 64 by a frictional fit between the socket 64 and the screw 100. As will be illustrated hereinafter, the socket 64 of the shaft 60 is configured for engaging with a capture 51 for pushing a capture with the rotational driver 35.

A first and a second slot 71 and 72 are located in the socket 64 at the distal end 62 of the shaft 60. The suture 10 extends from the screw 100 through the first and second slots 71 and 72 to the first and second suture retainers 41 and 42 for temporarily retaining the suture 10 with the socket 64.

FIGS. 8-11 are further views illustrating the rotational driver 35 of FIGS. 1-7. In this example of the invention, the socket is shown as a hexagonal socket for engaging with screw 100. The first and second slots 71 and 72 are located on opposed sides of the hexagonal socket 64. The edges of the first and second slots 71 and 72 are sharpened to form a first and a second cutting edge 81 and 82. The first and second cutting edges 81 and 82 are able to cut through bone tissue upon rotation of the rotational driver 35 while simultaneously insert the screw 100.

As best shown in FIGS. 10 and 11 a central orifice 90 is defined in the distal end 62 of the shaft 60. The central orifice 90 extends from a socket end 91 to a shaft end 92 located at an outer surface of the shaft 60 defining a tunnel 93 there between. The tunnel 93 positions a suture 10 centrally in the distal end 62 of the shaft 60. The tunnel 93 enables the suture 10 to be past through a capture 51 and through the tunnel 93 for enabling the rotational driver 35 to push the capture 51 along the suture 10.

FIGS. 12-15 are enlarged view illustrating the screw 100 of the present invention. The screw 100 comprises a screw body 102 having a helical screw thread shown as a canellous screw thread 104. The screw body 102 extends between a screw tip 106 and a screw head 110. The screw head 110 defines a socket shape in an outer periphery of the screw head 110 for enabling the socket 64 of the rotational driver 35 to rotationally insert the screw 100 into the living tissue 20. In this example, the screw head 110 is shown as having a cross-section of a regular polygon and in particular a regular hexagon.

A transverse aperture 115 extends through the screw body 102 of the screw 100. The transverse aperture 115 is perpendicular to an axis of rotation (not shown) extending from the screw tip 106 to the screw head 110.

A first and a second channel 121 and 122 are recessed into the outer periphery of the screw head 110 and allow for the insertion of the screw without a suture and by using a suture shuttle allow for a suture to be threaded through the embedded screw after implantation. In this example, the first and second channels 121 and 122 are recessed into opposed sides of the regular hexagon. The first and second channels 121 and 122 communicate with the transverse aperture 115 to form a screw pathway 125 for the suture 10. The first and second channels 121 and 122 and the transverse aperture 115 of the screw pathway 125 are dimensioned for enabling the suture 10 to be easily moved and or threaded through the screw pathway 125 while the screw body 102 including the screw head 110 is totally embedded into living tissue 20.

It should be appreciated by those skilled in the art that the screw 100 may take various forms and shapes and still obtain the benefit of the present invention. For example the length, size and shape of the screw body screw 102, the screw threads 104, the screw tip 106 as well as the screw head 110 may be varied depending upon the desired medical treatment. Furthermore, the screw pathway 125 comprising the first and second channels 121 and 122 and the transverse aperture 115 may take several shapes and sizes for enabling the suture 10 to be easily moved and or threaded through the screw pathway 125.

A specific example of the dimensions of the screw pathway 125 is shown in FIGS. 13 and 15 but should not be construed as being a limitation on the present invention. The distance [D] between opposed sides of the regular hexagon of the screw head 110 is shown in FIG. 15. Each of the first and second channels 121 and 122 has a recess depth [D/3] greater than one-third the distance [D] between opposed sides of the regular hexagon of the screw head 110. Each of the first and second channels 121 and 122 having a length greater than the distance [D] between opposed sides of the regular hexagon of the screw head 110.

Referring back to FIGS. 1-7, the first and second slots 71 and 72 of the distal end 62 of the shaft 60 are aligned with the first and second channels 121 and 12 of the screw head 110. The suture 10 extends through the screw pathway 125 comprising transverse aperture 115 and the first and second channels 121 and 122 of the screw 110 and into the first and second slots 71 and 72 of the shaft 60. The socket 64 is able to engage the outer periphery 112 of the screw head 110 when the suture 10 extends through the first and second channels 121 and 122 of the screw 110. Furthermore, the first and second channels 121 and 122 in the screw 100 permit the suture 10 to extend from the first and second slots 71 and 72 of the shaft through the first and second channels 121 and 122 and the transverse aperture 115 of the screw 100 whiles the first and second cutting edges 81 and 82 cut the bone 21 to countersink the head 110 of the screw 110 within the bone 21.

Figure 16:
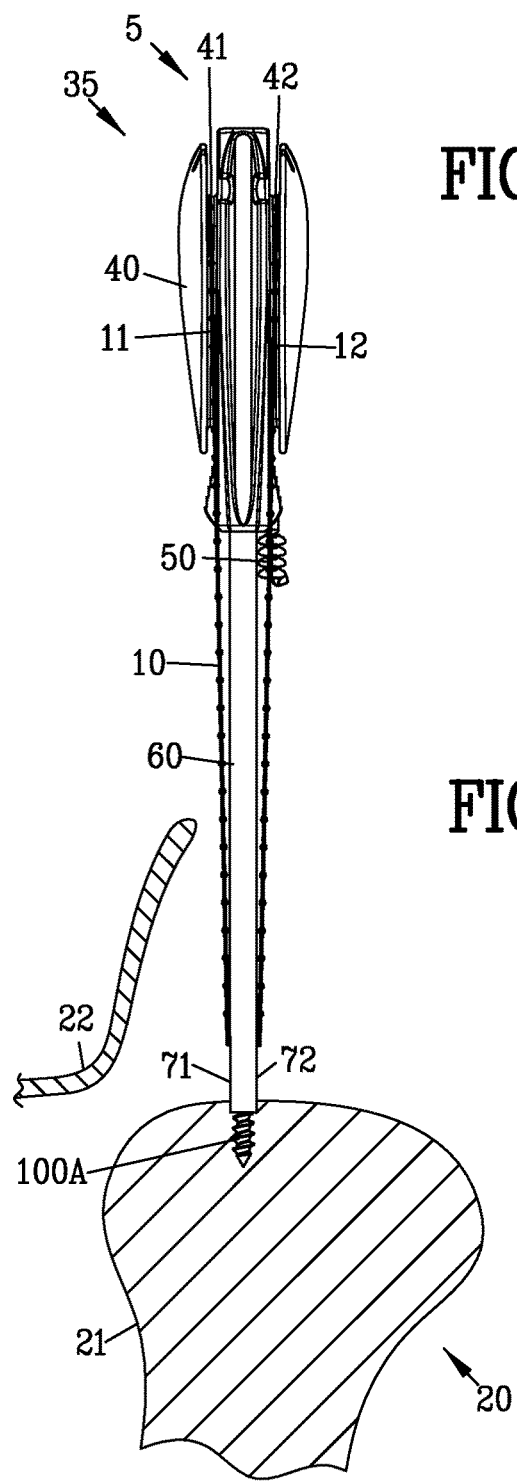
FIG. 16 illustrates a first step in securing a tissue to a bone including rotating the rotational driver with a suture for inserting a first screw with a suture into the bone and for cutting the bone to countersink the head of the screw.

FIG. 16 illustrates a first step in securing soft tissue 22 to a bone 21 including rotating the rotational driver 35 with the suture 10 for inserting the first screw 100A with the attached suture 10 into the bone 21 and for cutting the bone 21 to countersink the head 110 of the screw 100A.

Figure 17:
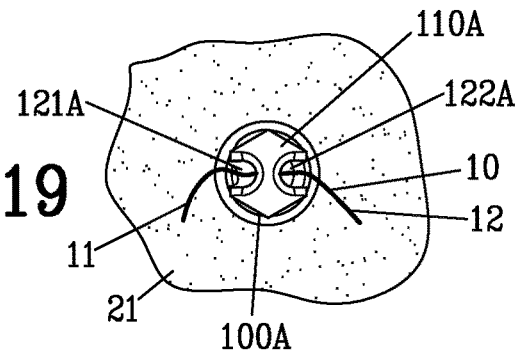
FIG. 17 is an enlarged view of the distal end of the rotational driver of FIG. 16 illustrating the cutting the bone to countersink the head of the first screw and then application of the capture so that the capture sits flush with the bone surface.

FIG. 17 is an enlarged view of the distal end of the rotational driver 35 of FIG. 16 illustrating the cutting the bone 21 to countersink the head 110 of the first screw 100A.

Figure 18:
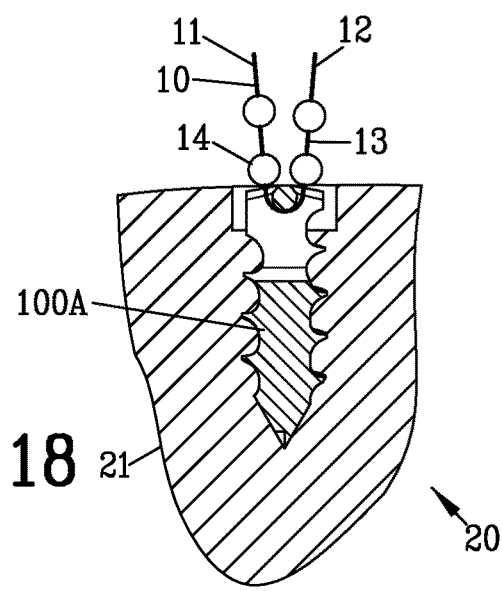
FIG. 18 is a view similar to FIG. 17 illustrating the free movement of the suture through a transverse aperture when the first screw is completely embedded into the bone.

FIG. 18 is a view similar to FIG. 17 illustrating the free movement of the suture 10 through the transverse aperture 115 when the first screw 100A is completely embedded into the bone 21.

Figure 19:
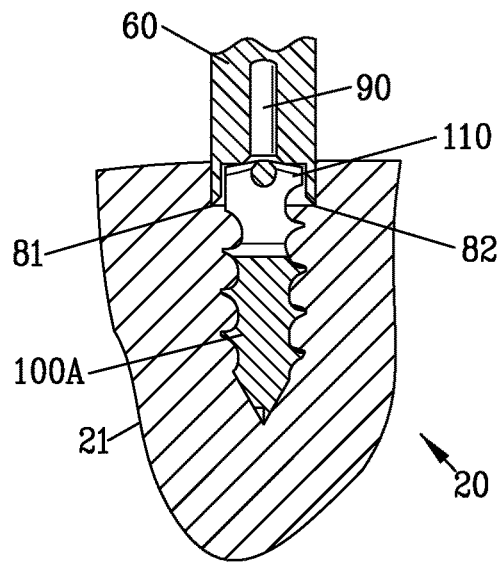
FIG. 19 is a top view of FIG. 18.

FIG. 19 is a top view of FIG. 18 further illustrating the free movement of the suture 10 through the transverse aperture 115.

Figure 20:
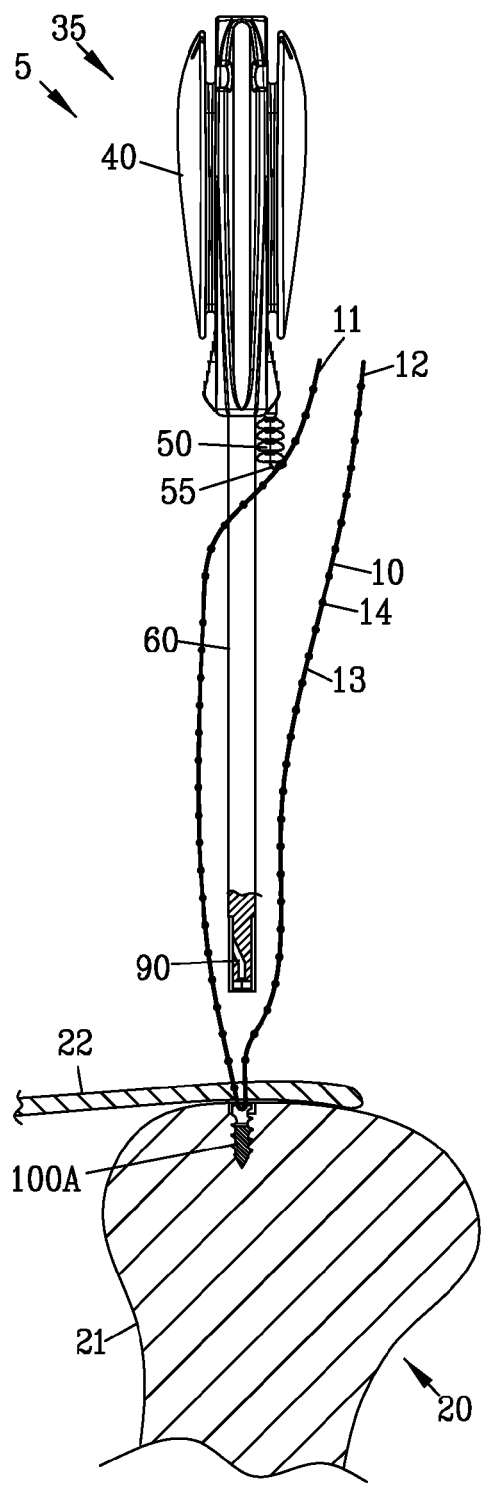
FIG. 20 illustrates the step of passing a first end of the suture through a resilient loop of a capture magazine for threading the first end of the suture through a capture aperture of a first capture.

FIG. 20 illustrates the step of passing the first end 11 of the suture 10 through the resilient loop 55 of a capture magazine 50 for threading the first end 11 of the suture 10 through a capture aperture 51X of a first capture 51. The suture 10 bends approximately one hundred and eighty degrees as the first capture 51 is removed from the resilient loop 55 to thread a loop of the suture 10 through the capture aperture 51X of a first capture 51.

Figure 21:
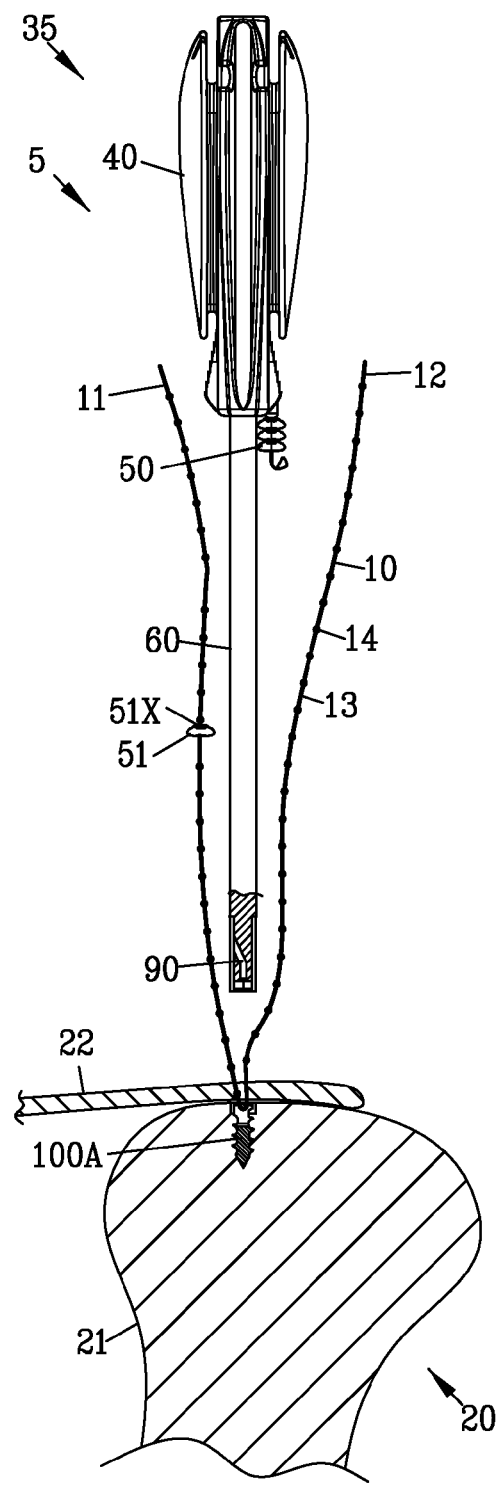
FIG. 21 illustrates the capture aperture of the first capture being moved along the suture.

FIG. 21 illustrates the capture aperture 51X of the first capture 51 being moved along the suture 10.

FIG. 22 illustrates the step of passing the first end 11 of the suture 10 through the central aperture 90 in the rotational driver 35.

FIG. 23 illustrates the step of pushing the capture 51 with the rotational driver 35 along the suture 10 to lockingly engage the capture 51 with one of the series of protuberances 14 for securing the first end 11 of the suture 10.

FIG. 24 is an enlarged view of a portion of FIG. 23 further illustrating the locking engagement of the capture 51 with one of the protuberances 14 of the suture 10.

Figures 25, 26, 27:
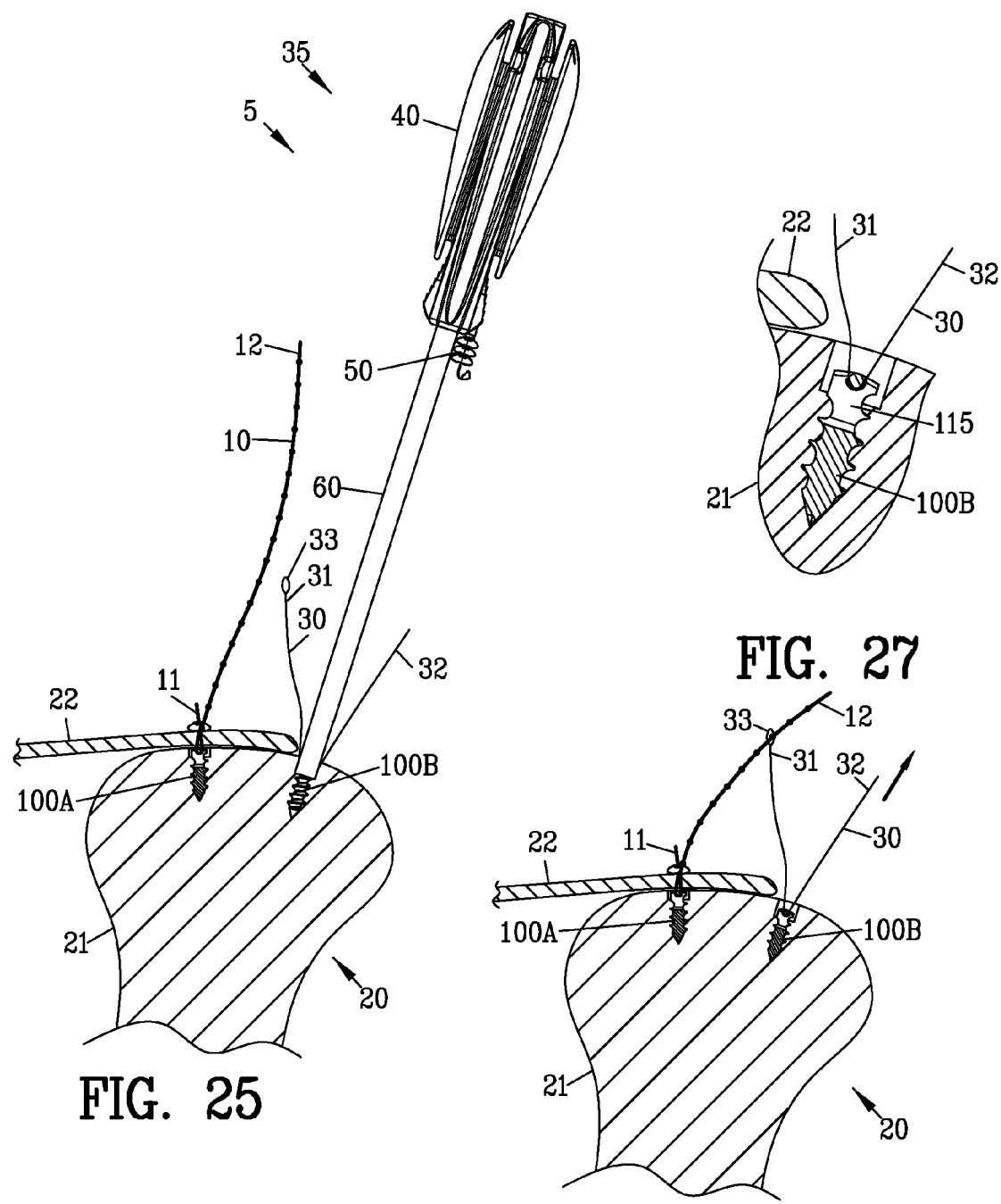
FIG. 25 illustrates the step of inserting a second screw and a suture shuttle into the bone and for cutting the bone to countersink the head of the second screw.
FIG. 26 illustrates the step of inserting a second end of the suture into the loop of the suture shuttle.
FIG. 27 is an enlarged view of FIG. 26 illustrating the free movement of the suture shuttle through a transverse aperture when the second screw is completely embedded into the bone.

FIG. 25 illustrates the step of inserting a second screw 100B and a suture shuttle 30 into the bone 21 and for cutting the bone 21 to countersink the head 110 of the second screw 100B. The suture shuttle 30 extends between a first end 31 and a second end 32 and has a loop 33 located at the first end 31. Preferably, the suture shuttle 30 is treaded through the transverse aperture 115 of the second screw 100B before the second screw 100B is inserted into the socket 64 of the rotational driver 35.

FIG. 26 illustrates the step of inserting a second end 12 of the suture 10 into the loop 33 of the suture shuttle 30.

FIG. 27 is an enlarged view of FIG. 26 illustrating the free movement of the suture shuttle 30 through a transverse aperture 115 when the second screw 100B is completely embedded into the bone 21.

Figures 28, 29, 30:
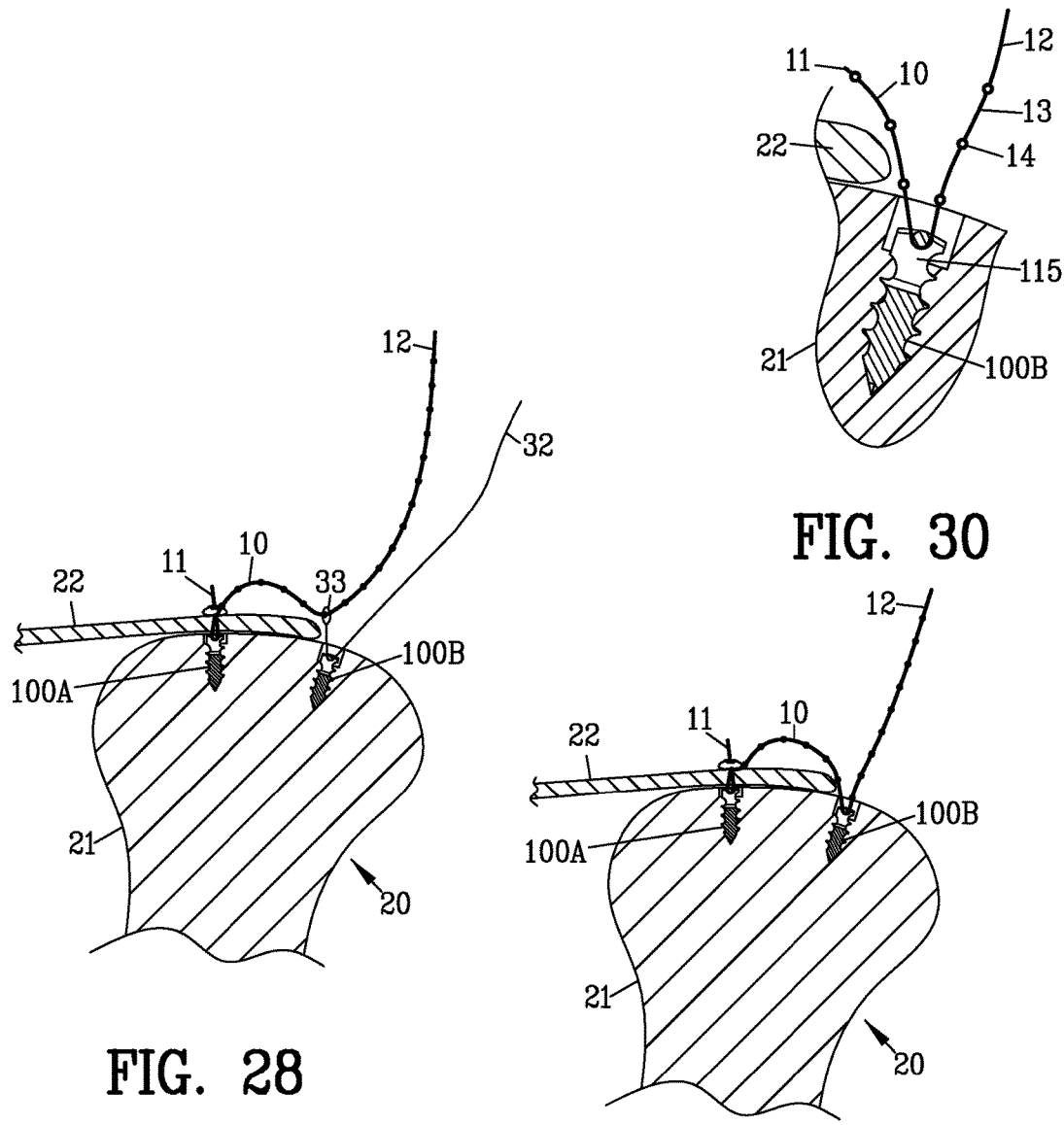
FIG. 28 illustrates the step of threading the second end of the suture through a transverse aperture of the second screw.
FIG. 29 illustrates the second end of the suture threaded through the transverse aperture of the second screw.
FIG. 30 is an enlarged view of a portion of FIG. 29.

FIG. 28 illustrates the step of threading the second end 12 of the suture 10 through the transverse aperture 115 of the second screw 100B. As the suture shuttle 30 is pulled through the transverse aperture 115 of the second screw 100B, the loop 33 bends the suture 10 approximately one hundred and eighty degrees to form a doubled up suture loop that is threaded through the transverse aperture 115 of the second screw 100B. The second channels 121 and 122 and the transverse aperture 115 are dimensioned for enabling the doubled up suture loop of the suture 10 to be easily threaded through the second screw 100B while the second screw 100B is totally embedded into the bone 21.

FIGS. 29 and 30 illustrates the second end 12 of the suture 10 threaded through the transverse aperture 115 of the second screw 100B. The suture 10 is free to move through the second screw 100B while the second screw 100 is totally embedded into the bone 21 in order to tighten the suture 10 to bring the soft tissue 22 into engagement with the bone 21.

Figures 31, 32:
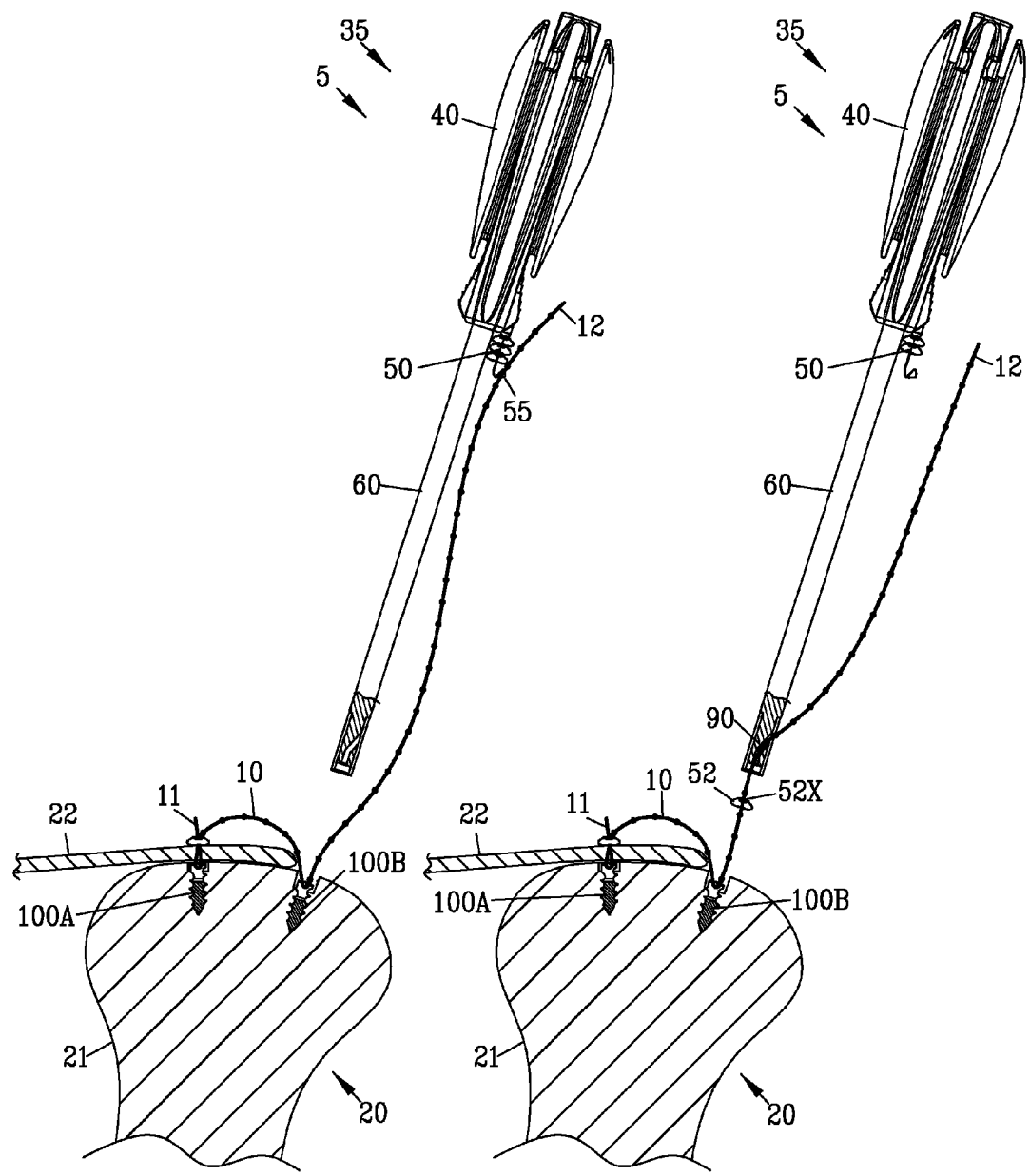
FIG. 31 illustrates the step of passing the second end of the suture through the resilient loop of the capture magazine for threading the second end of the suture through a capture aperture of a second capture.
FIG. 32 illustrates the step of passing the second end of the suture through a central aperture in the driver.

FIG. 31 illustrates the step of passing the second end 12 of the suture 10 through the resilient loop 55 of the capture magazine 50 for threading the second end 12 of the suture 10 through the capture aperture 52X of a second capture 52.

FIG. 32 illustrates the step of passing the second end 12 of the suture 10 through a central aperture 90 in the rotational driver 35 after the capture aperture 52X of the second capture 52 has been moved along the suture 10.

FIG. 33 illustrates the step of pushing the second capture 52 with the rotational driver 35 along the suture 10 to lockingly engage the second capture 51 with one of the series of protuberances 14 for securing the second end 12 of the suture 10.

FIGS. 34 and 35 illustrate the second capture 52 lockingly engaged with one of the series of protuberances 14 of the suture 10. The suture 10 was free to move through the second screw 100B while the second screw 100B was totally embedded into the bone 21 in order to tighten the suture 10 to bring the soft tissue 22 into engagement with the bone 21.

Figure 36:
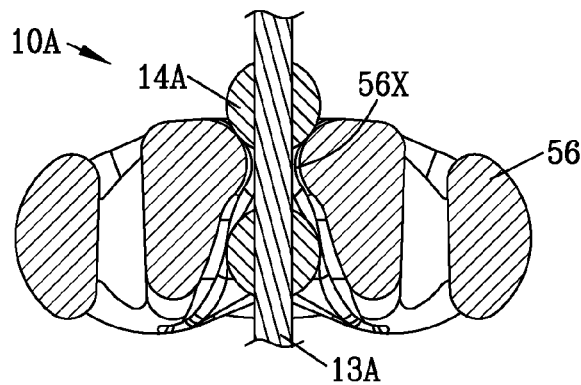
FIG. 36 is an isometric view of a first example of a suture having a series of protuberances engaging with a capture aperture of a capture.

FIG. 36 is an isometric view of a first example of a suture 10A having a series of protuberances 14A engaging with a capture aperture 56X of a capture 56. A full explanation of the operation and benefit of this capture may be found in PCT patent application PCT/U82013/063277 which is incorporated by reference as if fully set forth herein.

Figures 37, 38:
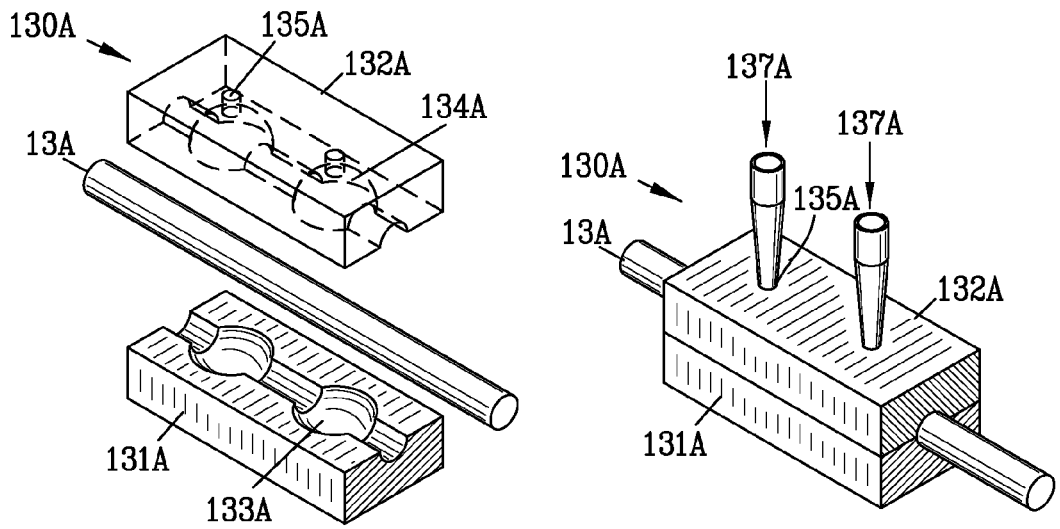
FIG. 37 is an isometric view of a first step in a method for forming a protuberance on a suture illustrating placing a suture to extend through a mold cavity.
FIG. 38 is an isometric view of a second step in the method for forming the protuberance on the suture illustrating inserting an adhesive into the mold cavity.

FIG. 37 is an isometric view of a first step in a method for forming a protuberance 14A on a suture 10A. The mold 130A comprises a first mold and a second mold 131A and 132A defining a first and a second mold cavity 133A and 134A. Feeder tubes 135A communicate with the mold cavity 135A for introducing an adhesive 137A one into the mold cavity 135A. A flexible suture component 13A is placed into the mold cavities 133A and 134A to extend through the mold cavity 130A.

FIG. 38 is an isometric view of a second step in the method for forming the protuberance 14A on the suture 10A illustrating inserting an adhesive 137A into the mold cavities 133A and 134A through the feeder tubes 135A.

Figure 39:
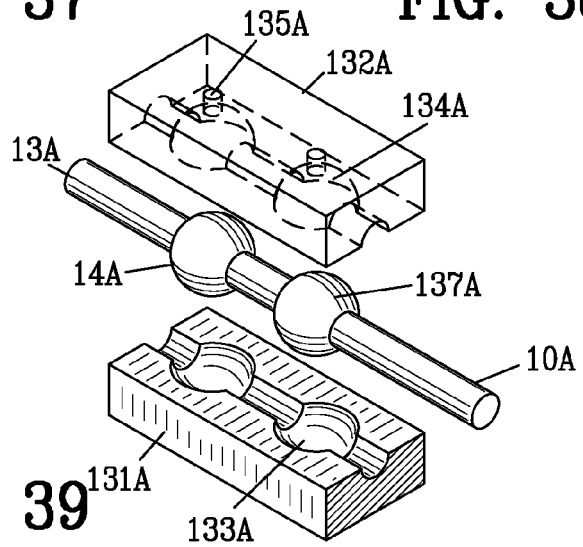
FIG. 39 is an isometric view of a third step in the method for forming the protuberance on the suture illustrating removing the suture with the adhered protuberance from the mold.

FIG. 39 is an isometric view of a third step in the method for forming the protuberance 14A on the suture 10A illustrating removing the suture 10A with the adhered protuberance 14A from the mold 130A. The protuberances 14A are formed entirely of the adhesive 137A.

Figure 40:
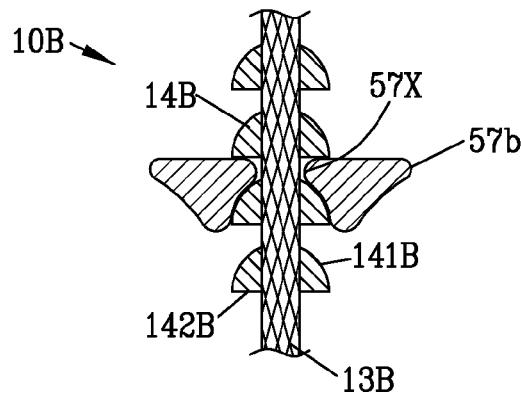
FIG. 40 is an isometric view of a second example of a suture having a series of protuberances engaging with a capture aperture of a capture.

FIG. 40 is an isometric view of a second example of a suture 10B having a series of protuberances 14B engaging with a capture aperture 57X of a capture 57. In this example, each of the protuberances 14B has a leading edge 141B and a trailing edge 142B. In contrast to the protuberances 14A shown in FIGS. 36-39, the leading edge 141B is not symmetrical with the trailing edge 142B. The non-symmetrical design of the protuberances 14B are specifically designed to engage with the specific capture at aperture 57X of a capture 57.

Figures 41, 42:
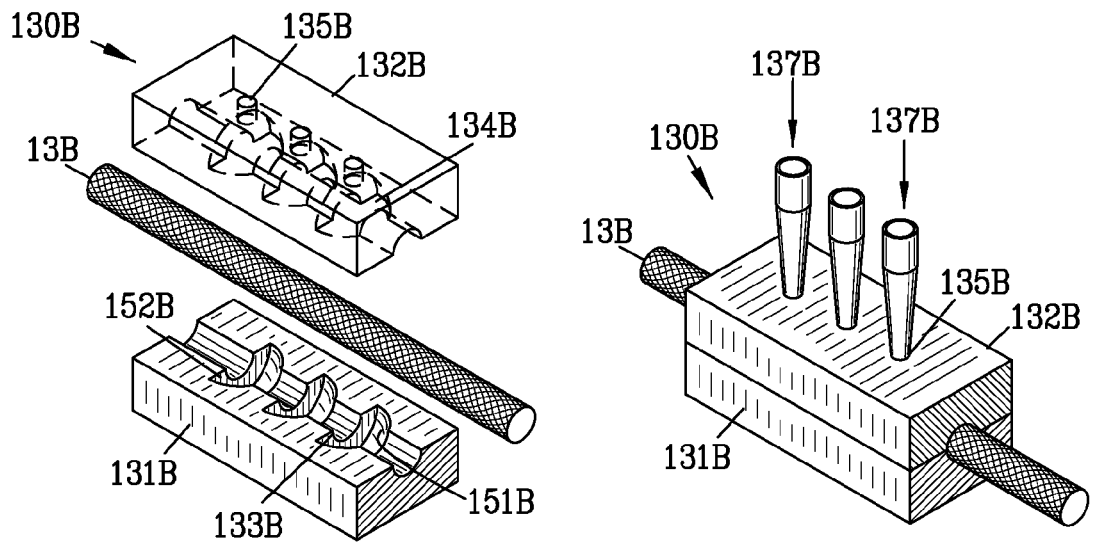
FIG. 41 is an isometric view of a first step in a method for forming a protuberance on a suture illustrating placing a suture into a mold having a series of mold cavities with each of the mold cavities having a leading edge and a trailing edge contoured for a specific capture.
FIG. 42 is an isometric view of the step of inserting an adhesive into the mold.

FIG. 41 is an isometric view of a first step in a method for forming a protuberance 14B on a suture 10B. The mold 130B comprises a first mold and a second mold 131B and 132B defining a first and a second mold cavity 133B and 134B.

The first and second mold cavity 133B and 134B define a leading mold portion 151B and a trailing mold portion 152B. The leading mold portion and trailing mold portion 151B and 152B correspond to the leading edge 141B and the trailing edge 142B of the protuberances 14B. Feeder tubes 135B communicate with the mold cavity 130B for introducing an adhesive 137B into the mold cavity 130B. A flexible suture component 13B is placed into the mold cavities 133B and 134B to extend through the mold cavity 130B.

FIG. 42 is an isometric view of a second step in the method for forming the protuberance 14B on the suture 10B illustrating inserting an adhesive 137B into the mold cavities 133B and 134B through the feeder tubes 135B.

Figure 43:
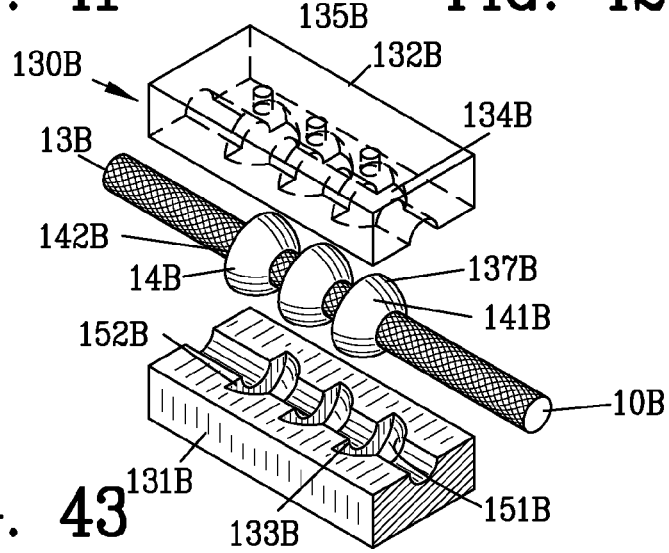
FIG. 43 is an isometric view of the step of removing the suture with the adhered protuberance from the mold.

FIG. 43 is an isometric view of a third step in the method for forming the protuberance 14B on the suture 10B illustrating removing the suture 10B with the adhered protuberance 14B from the mold 130B. The protuberances 14B are formed entirely of the adhesive 137B.

FIGS. 44-51 are sectional views of example of protuberances 14C-14J formed on a suture 10C-10J. Similar parts are labeled with similar reference numerals and added alphabetical character. Each of the suture 10C-10J include a flexible suture component 13C-13J which is the bent, shaped or tied to stabilize the protuberances 14C-14J formed solely from an adhesive 137. The bend shape or knot of the flexible suture component 13C-13J provides mechanical strength and prevent slippage of the protuberances 14C-14J.

FIGS. 36-43 illustrate a specific molding process for forming the protuberances 14 on a flexible suture component 13 for providing the suture 10. It should be understood that various other molding processes and or techniques may be utilized for forming the protuberances 14 on a flexible suture component 13. For example, various adhesives may be used as well as various types of molding techniques such as waffle style and clam shell molds made of metal PTFE, or TEFLON as well as 3-D printing and the like.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An improved fastener for insertion into a living tissue by a driver, the driver having an older circumference surrounding a driver socket, the driver having opposed slots extending through the outer circumference and communicating with the driver socket for preloading a suture shuttle, comprising; a screw comprising a screw body and a screw head; said screw body having a helical screw thread extending from a screw tip and terminating at said screw head; said screw head defining a socket shape in an outer periphery of said screw head for engagement with the driver socket of the driver to insert said screw body into the living tissue; a first and a second axial channel recessed, defined in opposed sides of said screw head and extending into said helical screw thread in said screw body; a transverse aperture extending through said screw body and said screw head and intersecting said first and second axial channels; the opposed slots of the driver being aligned with said first and a second axial channel for enabling the suture shuttle to extend through the opposed slots of the driver and said first and second axial channels and said transverse aperture while said screw body is inserted totally into the living tissue; said first and second channels and said transverse aperture being dimensioned tor enabling the suture shuttle to be moved through said first and second channels and said transverse aperture for threading a suture through the first and second channels and said transverse aperture after said screw body is totally embedded into the living tissue; and said first and second channels being recessed into opposed sides of said screw head; each of said first and second channels having a recess depth greater than one-third the distance between opposed sides of the screw head; and each of said first and second channels having a length three times greater than said recess depth of each of said first and second channels.

2. An improved fastener for insertion into a living tissue as set forth in claim 1, wherein said socket shape extends a maximum lateral distance substantially equal to said maximum thread diameter of said helical screw thread.

3. An improved fastener for insertion into a living tissue as set forth in claim 1, wherein said screw head has a maximum apex to apex diameter substantially equal to said maximum thread diameter of said helical screw thread.

4. An improved fastener for insertion into a living tissue as set forth in claim 1, wherein said helical screw thread having an outer circumference substantially equal to the outer circumference the driver.

5. Am improved fastener for insertion into a living tissue by a driver, the driver having an outer circumference surrounding a driver socket, the driver having opposed slots extending through the outer circumference and communicating with the driver socket for preloading a suture, comprising: a screw comprising a screw body and a screw head; said screw body having a helical screw thread extending from a screw tip and terminating at said screw head; said screw head defining a socket shape in an outer periphery of said screw head for engagement with, the driver socket of the driver to insert said screw body into the living tissue; a first and a second axial channel recessed defined in opposed sides of said screw head and extending into said helical screw thread in said screw body; a transverse aperture extending through said screw body and said screw head and intersecting said first and second axial channels; the opposed slots of the driver being aligned with said first and a second axial channel for enabling the suture to extend through the opposed slots of the driver and said first and second axial channels and said transverse aperture while said screw body is inserted totally into the living tissue; said first and second channels and said transverse aperture being dimensioned for enabling the suture to be moved through said first and second channels and said transverse aperture after said screw body is totally embedded into the living tissue; and said first and second channels being recessed into opposed sides of said screw head; each of said first and second channels having a recess depth greater than one-third the distance between opposed sides of the screw head; and each of said first and second channels having a length three times greater than said recess depth of each of said first and second channels.

6. An improved fastener for insertion into a living tissue as set forth in claim 5, wherein said socket shape extends a maximum lateral distance substantially equal to said maximum thread diameter of said helical screw thread.

7. An improved fastener for insertion into a living tissue as set forth in claim 5, wherein said screw head has a maximum apex to apex diameter substantially equal to said maximum thread diameter of said helical screw thread.

8. An improved fastener for insertion into a living tissue as set forth in claim 5, wherein said helical screw thread having an outer circumference substantially equal to the outer circumference the driver.

* * * * *